(12) United States Patent
Mandelbaum et al.

(10) Patent No.: US 12,420,085 B2
(45) Date of Patent: Sep. 23, 2025

(54) SYNERGISTIC THERAPIES FOR INTER VERTEBRAL DISC DEGENERATION

(71) Applicant: DISCURE TECHNOLOGIES LTD., Herzeliya (IL)

(72) Inventors: Yuval Mandelbaum, Gat-Rimon (IL); Yossi Gross, Moshav Mazor (IL); Yehuda Zadok, Kiryat Ono (IL)

(73) Assignee: Discure Technologies Ltd, Herzliya (IL)

( * ) Notice: Subject to any disclaimer, the term of this patent is extended or adjusted under 35 U.S.C. 154(b) by 250 days.

(21) Appl. No.: 17/693,938

(22) Filed: Mar. 14, 2022

(65) Prior Publication Data

US 2022/0347464 A1    Nov. 3, 2022

Related U.S. Application Data

(63) Continuation of application No. 17/306,209, filed on May 3, 2021, now Pat. No. 11,298,530.

(51) Int. Cl.
| | | |
|---|---|---|
| *A61N 1/32* | (2006.01) | |
| *A61K 9/00* | (2006.01) | |
| *A61K 35/12* | (2015.01) | |
| *A61K 35/28* | (2015.01) | |
| *A61K 35/30* | (2015.01) | |

(Continued)

(52) U.S. Cl.
CPC .......... *A61N 1/0551* (2013.01); *A61K 9/0004* (2013.01); *A61K 9/0009* (2013.01); *A61K 35/12* (2013.01); *A61K 35/28* (2013.01); *A61K 35/30* (2013.01); *A61K 47/02* (2013.01);

(Continued)

(58) Field of Classification Search
CPC ........ A61N 1/205; A61N 1/306; A61N 1/325; A61N 1/326; A61N 1/327
See application file for complete search history.

(56) References Cited

U.S. PATENT DOCUMENTS

| | | |
|---|---|---|
| 4,044,774 A | 8/1977 | Corbin et al. |
| 4,360,031 A | 11/1982 | White |

(Continued)

FOREIGN PATENT DOCUMENTS

| | | |
|---|---|---|
| JP | 2004-321242 | 11/2004 |
| JP | 2007-501067 | 1/2007 |

(Continued)

OTHER PUBLICATIONS

Non-Final Office Action dated Oct. 28, 2021 issued in U.S. Appl. No. 17/402,911.

(Continued)

*Primary Examiner* — Deanna K Hall
(74) *Attorney, Agent, or Firm* — Sughrue Mion, PLLC

(57) ABSTRACT

A method for treating an intervertebral disc of a subject is provided, the method including delivering a growth factor to a nucleus pulposus of the intervertebral disc. At least one intra-pulposus exposed electrode surface is implanted in the nucleus pulposus. At least one extra-pulposus exposed electrode surface is implanted in a body of the subject outside the nucleus pulposus. The growth factor is supported by activating control circuitry to drive the intra-pulposus and the extra-pulposus exposed electrode surfaces to electroosmotically drive nutrient-containing fluid into the nucleus pulposus. Other embodiments are also described.

15 Claims, 18 Drawing Sheets

(51) Int. Cl.
   *A61K 47/02*      (2006.01)
   *A61K 47/26*      (2006.01)
   *A61N 1/05*       (2006.01)

(52) U.S. Cl.
   CPC .............. *A61K 47/26* (2013.01); *A61N 1/32* (2013.01); *A61N 1/325* (2013.01)

(56) References Cited

U.S. PATENT DOCUMENTS

| | | |
|---|---|---|
| 4,503,863 A | 3/1985 | Katims |
| 4,602,638 A | 7/1986 | Adams |
| 4,710,174 A | 12/1987 | Moden et al. |
| 4,738,250 A | 4/1988 | Fulkerson et al. |
| 5,088,977 A | 2/1992 | Sibalis |
| 5,121,754 A | 6/1992 | Mullett |
| 5,433,739 A | 7/1995 | Sluijter et al. |
| 5,529,574 A | 6/1996 | Frackelton |
| 5,792,100 A | 8/1998 | Shantha |
| 5,911,223 A | 6/1999 | Weaver et al. |
| 5,938,690 A | 8/1999 | Law et al. |
| 6,041,252 A | 3/2000 | Walker et al. |
| 6,146,380 A | 11/2000 | Racz et al. |
| 6,161,047 A | 12/2000 | King et al. |
| 6,360,750 B1 | 3/2002 | Gerber et al. |
| 6,567,702 B1 | 5/2003 | Nekhendzy et al. |
| 6,591,138 B1 | 7/2003 | Fischell et al. |
| 6,602,248 B1 | 8/2003 | Sharps et al. |
| 6,620,155 B2 | 9/2003 | Underwood et al. |
| 6,832,115 B2 | 12/2004 | Borkan |
| 6,941,172 B2 | 9/2005 | Nachum |
| 6,997,941 B2 | 2/2006 | Sharkey et al. |
| 7,013,177 B1 | 3/2006 | Whitehurst et al. |
| 7,069,083 B2 | 6/2006 | Finch et al. |
| 7,120,489 B2 | 10/2006 | Shalev et al. |
| 7,155,287 B2 | 12/2006 | Gavronsky |
| 7,174,221 B1 | 2/2007 | Chen et al. |
| 7,217,351 B2 | 5/2007 | Krumme |
| 7,223,227 B2 | 5/2007 | Pflueger |
| 7,270,659 B2 | 9/2007 | Ricart et al. |
| 7,317,947 B2 | 1/2008 | Wahlstrand et al. |
| 7,398,121 B2 | 7/2008 | Matsumura et al. |
| 7,509,171 B2 | 3/2009 | DiMauro |
| 7,640,062 B2 | 12/2009 | Shalev |
| 7,831,306 B2 | 11/2010 | Finch et al. |
| 7,860,569 B2 | 12/2010 | Solberg et al. |
| 8,060,207 B2 | 11/2011 | Wallace et al. |
| 8,190,248 B2 | 5/2012 | Besio et al. |
| 8,366,615 B2 | 2/2013 | Razavi |
| 8,457,761 B2 | 6/2013 | Wariar |
| 8,577,469 B2 | 11/2013 | Gross |
| 8,676,348 B2 * | 3/2014 | Gross .................. A61N 1/205 607/117 |
| 8,740,982 B2 | 6/2014 | Lee |
| 9,005,289 B1 | 4/2015 | Simionescu et al. |
| 9,131,980 B2 | 9/2015 | Bloom |
| 9,616,221 B2 | 4/2017 | Gross |
| 9,724,513 B2 | 8/2017 | Lane et al. |
| 9,731,122 B2 | 8/2017 | Gross |
| 10,398,884 B2 | 9/2019 | Lad et al. |
| 10,765,527 B2 | 9/2020 | Chin et al. |
| 11,376,021 B2 * | 7/2022 | Marino .............. A61B 17/1671 |
| 2002/0151948 A1 | 10/2002 | King et al. |
| 2002/0183683 A1 | 12/2002 | Lerner |
| 2003/0130707 A1 | 7/2003 | Gan et al. |
| 2003/0158589 A1 | 8/2003 | Katsnelson |
| 2003/0216792 A1 | 11/2003 | Levin et al. |
| 2003/0225331 A1 | 12/2003 | Diederich et al. |
| 2004/0002746 A1 | 1/2004 | Ryan et al. |
| 2004/0019381 A1 | 1/2004 | Pflueger |
| 2004/0049180 A1 | 3/2004 | Sharps et al. |
| 2004/0083002 A1 | 4/2004 | Belef et al. |
| 2004/0116977 A1 | 6/2004 | Finch et al. |
| 2004/0186576 A1 | 9/2004 | Biscup et al. |
| 2004/0210209 A1 * | 10/2004 | Yeung ................ A61B 17/7061 604/500 |
| 2005/0010205 A1 | 1/2005 | Hovda et al. |
| 2005/0021104 A1 | 1/2005 | DiLorenzo |
| 2005/0119650 A1 | 6/2005 | Sanders et al. |
| 2005/0137646 A1 | 6/2005 | Wallace et al. |
| 2005/0137647 A1 | 6/2005 | Wallace et al. |
| 2005/0159790 A1 | 7/2005 | Shalev |
| 2005/0187589 A1 | 8/2005 | Wallace et al. |
| 2005/0203599 A1 | 9/2005 | Garabedian et al. |
| 2005/0203600 A1 | 9/2005 | Wallace et al. |
| 2005/0203602 A1 | 9/2005 | Wallace et al. |
| 2005/0222647 A1 | 10/2005 | Wahlstrand et al. |
| 2005/0277996 A1 | 12/2005 | Podhajsky et al. |
| 2006/0030895 A1 * | 2/2006 | Simon .................. A61N 1/40 607/43 |
| 2006/0106430 A1 | 5/2006 | Fowler et al. |
| 2006/0224223 A1 | 10/2006 | Podhajsky et al. |
| 2006/0293723 A1 | 12/2006 | Whitehurst et al. |
| 2007/0000784 A1 | 1/2007 | Paul et al. |
| 2007/0073402 A1 | 3/2007 | Vresilovic et al. |
| 2007/0162086 A1 | 7/2007 | Dilorenzo |
| 2007/0213700 A1 | 9/2007 | Davison et al. |
| 2007/0233202 A1 | 10/2007 | Wallace et al. |
| 2007/0255338 A1 | 11/2007 | Wahlstrand |
| 2007/0276201 A1 | 11/2007 | Lee et al. |
| 2008/0009927 A1 | 1/2008 | Vilims |
| 2008/0119907 A1 | 5/2008 | Stahmann |
| 2008/0177392 A1 | 7/2008 | Williams et al. |
| 2008/0260542 A1 | 10/2008 | Nishikawa et al. |
| 2009/0030399 A1 | 1/2009 | Raiszadeh |
| 2009/0062885 A1 | 3/2009 | Brighton et al. |
| 2009/0112278 A1 | 4/2009 | Wingeier et al. |
| 2009/0125080 A1 | 5/2009 | Montgomery |
| 2009/0126813 A1 | 5/2009 | Yanagisawa et al. |
| 2009/0131850 A1 | 5/2009 | Geiger |
| 2009/0216113 A1 | 8/2009 | Meier et al. |
| 2009/0312816 A1 | 12/2009 | Gross |
| 2010/0057204 A1 | 3/2010 | Kadaba et al. |
| 2010/0100185 A1 | 4/2010 | Trieu et al. |
| 2010/0131067 A1 | 5/2010 | Metcalf, Jr. et al. |
| 2010/0217369 A1 | 8/2010 | Gross |
| 2010/0324441 A1 | 12/2010 | Hargrove et al. |
| 2011/0046540 A1 | 2/2011 | Alterman et al. |
| 2011/0054518 A1 | 3/2011 | Carbunaru et al. |
| 2011/0066192 A1 | 3/2011 | Frasier et al. |
| 2011/0125158 A1 | 5/2011 | Diwan et al. |
| 2011/0160638 A1 | 6/2011 | Mauge et al. |
| 2011/0160797 A1 | 6/2011 | Makous et al. |
| 2011/0270399 A1 | 11/2011 | Yurek et al. |
| 2012/0041562 A1 | 2/2012 | Shachar et al. |
| 2012/0053659 A1 | 3/2012 | Molnar et al. |
| 2012/0100607 A1 | 4/2012 | Duntsch et al. |
| 2012/0191159 A1 | 7/2012 | Willeford |
| 2012/0203307 A1 | 8/2012 | Schroeppel et al. |
| 2013/0066392 A1 | 3/2013 | Simon et al. |
| 2013/0102952 A1 | 4/2013 | Gross |
| 2013/0166006 A1 | 6/2013 | Williams |
| 2013/0289385 A1 | 10/2013 | Lozano et al. |
| 2013/0289599 A1 | 10/2013 | Yeung et al. |
| 2014/0058189 A1 | 2/2014 | Stubbeman |
| 2014/0088672 A1 | 3/2014 | Bedenbaugh |
| 2014/0207224 A1 | 7/2014 | Simon |
| 2014/0257168 A1 | 9/2014 | Gill |
| 2014/0324128 A1 | 10/2014 | Gross |
| 2015/0011927 A1 | 1/2015 | Hua |
| 2015/0119898 A1 | 4/2015 | Desalles et al. |
| 2016/0220699 A1 | 8/2016 | O'Heeron |
| 2016/0331970 A1 | 11/2016 | Lozano |
| 2016/0354541 A1 | 12/2016 | Crawford et al. |
| 2017/0007823 A1 | 1/2017 | Gross |
| 2017/0120053 A1 | 5/2017 | Fostick et al. |
| 2017/0274207 A1 | 9/2017 | Gross |
| 2018/0071523 A1 | 3/2018 | Gross et al. |
| 2018/0207004 A1 | 7/2018 | Yeung et al. |

FOREIGN PATENT DOCUMENTS

| | | |
|---|---|---|
| WO | 94/05369 | 3/1994 |
| WO | 01/52931 | 7/2001 |
| WO | 01/85027 | 11/2001 |

(56) References Cited

FOREIGN PATENT DOCUMENTS

| WO | 2001/085094 | 11/2001 |
|---|---|---|
| WO | 2005/011805 | 2/2005 |
| WO | 2006/090397 | 8/2006 |
| WO | 2008/007369 | 1/2008 |
| WO | 2017/072769 | 5/2017 |

OTHER PUBLICATIONS

Non-Final Office Action dated Jul. 27, 2021 issued in U.S. Appl. No. 17/306,209.
Karran September E et201 al., 1 "The Amyloid cascade hypothesis for AD," Nature Reviews Drug Discovery, vol. 10; 698-712.
De La Torre JC, "Vascular Basis of Alzheimer's Pathogensis," Ann NY Acad Sci. 977:196-215 (Nov. 2002).
Weller RO et al, "Perivascular Drainage of Amyloid-b Peptides from the Brain and Its Failure in Cerebral Amyloid Angiopathy and Alzheimer's Disease," Brain Pathology 18 (Apr. 2008) 253-266.
Brief PubMed search for metal ions in Alzheimers.
An Office Action dated Sep. 27, 2016, which issued during the prosecution of U.S. Appl. No. 14/926,705.
An International Search Report and a Written Opinion both dated August 7. 2008, which issued during the prosecution of Applicant's PCT/IL2007/000865.
An Office Action dated Mar. 29, 2013, which issued during the prosecution of U.S. Appl. No. 12/373,306.
An Office Action dated Oct. 31, 2011, which issued during the prosecution of U.S. Appl. No. 12/373,306.
An Office Action dated Oct. 1, 2012, which issued during the prosecution of U.S. Appl. No. 12/373,306.
Notice of Allowance dated Jul. 24, 2013, which issued during the prosecution of U.S. Appl. No. 12/663,306.
An Office Action dated Apr. 11, 2013, which issued during the prosecution of U.S. Appl. No. 13/663,757.
Notice of Allowance dated Oct. 28, 2013, which issued during the prosecution of U.S. Appl. No. 13/663,757.
Elixmann IM et al., "In-vitro evaluation of a drainage catheter with integrated bioimpedance electrodes to determine ventricular size," Biomed Tech 2013; 58 (Suppl. 1) Sep. 2013 (2 pages total).
An Office Action dated Aug. 31, 2015, which issued during the prosecution of U.S. Appl. No. 13/872,794.
An Applicant Initiated Interview Summary dated Dec. 14, 2015, which issued during the prosecution of U.S. Appl. No. 13/872,794.
An Office Action dated Feb. 3, 2016, which issued during the prosecution of U.S. Appl. No. 13/872,794.
Notice of Allowance dated Dec. 9, 2016, which issued during the prosecution of U.S. Appl. No. 14/794,739.
An Applicant Initiated Interview Summary dated Feb. 25, 2016, which issued during the prosecution of U.S. Appl. No. 13/872,794.
An Office Action dated Jun. 15, 2016, which issued during the prosecution of U.S. Appl. No. 13/872,794.
An International Search Report and a Written Opinion both dated Oct. 20. 2016, which issued during the prosecution of Applicant's PCT/IL2016/050728.
An Office Action dated Sep. 21, 2016, which issued during the prosecution of U.S. Appl. No. 14/794,739.
An International Search Report and a Written Opinion both dated Jan. 26. 2017, which issued during the prosecution of Applicant's PCT/IL2016/051161.
Notice of Allowance dated Jul. 14. 2017, which issued during the prosecution of U.S. Appl. No. 13/872,794.
An Office Action dated May 26. 2017, which issued during the prosecution of U.S. Appl. No. 15/453,290.
An International Preliminary Report on Patentability dated Apr. 7, 2009, which issued during the prosecution of Applicant's PCT/IL2007/000865.
Loutzenhiser, "Membrane Potential measurements in renal afferent and efferent arterioles: actions of Angiotensin II", AJP—Renal Physiol Aug. 1, 1997 vol. 273 No. 2 F307-F314.
U.S. Appl. No. 60/830,717, filed Jul. 12, 2006.

Dao-Sheng Liu et al., "Activation of Na+ and K+ Pumping Modes of (Na,K)—ATPase by an Oscillating Electric Field," The Journal of Biological Chemistry, vol. 265. No. 13, May 5, 1990. (pp. 7260-7267).
Robert F. Service.. "Electric fields deliver druas into tumors." http://news.sciencemaa.ora. Feb. 4, 2015. (5 Pages Total).
Vernengo J, "Injectable Bioadhesive Hydrogels for Nucleus Pulposus Replacement and Repair of the Damaged Intervertebral Disc: A Thesis," Drexel University (Jan. 2007).
Urban JPG et al., "The nucleus of the intervertebral disc from development to degeneration," American Zoologist 40(1): 53-61 (2000).
Cheung KMC et al., "Intervertebral disc regeneration by use of autologous mesenchymal stem cells, an experimental model in rabbits," Abstract from the SRS 2004 Annual Meeting.
Freemont TJ et al., "Degeneration of intervertebral discs: current understanding of cellular and molecular events, and implications for novel therapies," Expert Reviews in Molecular Biology, Mar. 29, 2001 (Cambridge University Press).
An Office Action dated Sep. 12, 2011, which issued during the prosecution of U.S. Appl. No. 12/373,306.
An Office Action dated Jul. 24, 2017, which issued during the prosecution of U.S. Appl. No. 14/982,187.
An International Search Report and a Written Opinion both dated Mar. 10, 2017, which issued during the prosecution of Applicant's PCT/IL2016/051363.
An Office Action dated Mar. 25, 2019, which issued during the prosecution of U.S. Appl. No. 15/742,245.
An Office Action together with the English translation dated Aug. 19, 2020, which issued during the prosecution of Japanese Patent Application No. 2018-521586.
An Office Action dated Apr. 25, 2018, which issued during the prosecution of U.S. Appl. No. 15/637,330.
An Office Action dated Nov. 20, 2020, which issued during the prosecution of U.S. Appl. No. 16/353,407.
An Office Action dated Jan. 22. 2020, which issued during the prosecution of U.S. Appl. No. 15/771,551.
An Office Action dated Nov. 29, 2019, which issued during the prosecution of U.S. Appl. No. 15/969,411.
An International Search Report and a Written Opinion both dated May 23, 2019, which issued during the prosecution of Applicant's PCT/IL2019/050284.
An Office Action dated Jul. 29, 2019, which issued during the prosecution of U.S. Appl. No. 15/618,325.
An Office Action dated Mar. 6, 2020, which issued during the prosecution of U.S. Appl. No. 15/618,325.
Sawyer PN et al., "Measurement of streaming potentials of mammalian blood vessels, aorta and venacava, in vivo," Biophysical journal vol. 6,5 (1966): 641-51. doi:10.1016/50006-3495(66)86683-3.
Acupuncture Injection Therapy _ Pain Arthritis Relief Center, first viewed Sep. 2020.
"Researchers developing biomaterial to treat spinal disc degeneration," Medical Press, Jun. 13, 2019 (2019-06-biomaterial-spinal-disc-degeneration).
Avista™ MRI xx cm 8 Contact Lead Kit: Directions for Use, Boston Scientific, Apr. 2016 (91063583-01_RevC_Avista_MRI_Lead_DFU_en-USA_S).
Akbarzadeh, Abolfazl, et al. "Liposome: classification, preparation, and applications." Nanoscale research letters 8.1 (2013): 1-9.
Herrlich, Simon, et al. "Drug release mechanisms of steroid eluting rings in cardiac pacemaker lead electrodes." Engineering in Medicine and Biology Society (EMBC), 2012 Annual International Conference of the IEEE. IEEE, 2012.
Freemont, A. J., et al. "Nerve In-Growth Into Painful Intervertebral Discs is Mediated by Nerve Growth Factor Roduced by Endothelial Cells of Local Blood Vessels." Orthopaedic Proceedings. vol. 84. No. SUPP_II. The British Editorial Society of Bone & Joint Surgery, 2018.
Dolor, Aaron, et al. "Matrix modification for enhancing the transport properties of the human cartilage endplate to improve disc nutrition." PloS one 14.4 (2019): e0215218.

(56) References Cited

OTHER PUBLICATIONS

Bowles, Robert D., and Lori A. Setton. "Biomaterials for intervertebral disc regeneration and repair." Biomaterials 129 (2017): 54-67.
Kang, James D. "Commentary on "Gene Therapy Approach for Intervertebral Disc Degeneration: An Update"." Neurospine 17.1 (2020): 15-16.
Liang, C., et al. "New hypothesis of chronic back pain: low pH promotes nerve ingrowth into damaged intervertebral disks." Acta Anaesthesiologica Scandinavica 57.3 (2013): 271-277.
Lee, Ho-Jin, et al. "Effectiveness of continuous hypertonic saline infusion with an automated infusion pump for decompressive neuroplasty: a randomized clinical trial." The Korean journal of pain 32.3 (2019): 196.
An Office Action dated Feb. 16, 2021, which issued during the prosecution of U.S. Appl. No. 16/558,987.
Takeoka, Yoshiki, Takashi Yurube, and Kotaro Nishida. "Gene therapy approach for intervertebral disc degeneration: An update." Neurospine 17.1 (2020): 3.
Sobajima, S., et al. "Gene therapy for degenerative disc disease." Gene therapy 11.4 (2004): 390-401.
Sato, Kimiaki, Kensei Nagata, and Teruyuki Hirohashi. "Intradiscal pressure after repeat intradiscal injection of hypertonic saline: an experimental study." European Spine Journal 11.1 (2002): 52-56.
Meisel, Hans-Joerg, et al. "Cell therapy for treatment of intervertebral disc degeneration: a systematic review." Global spine journal 9.1_suppl (2019): 39S-52S.

* cited by examiner

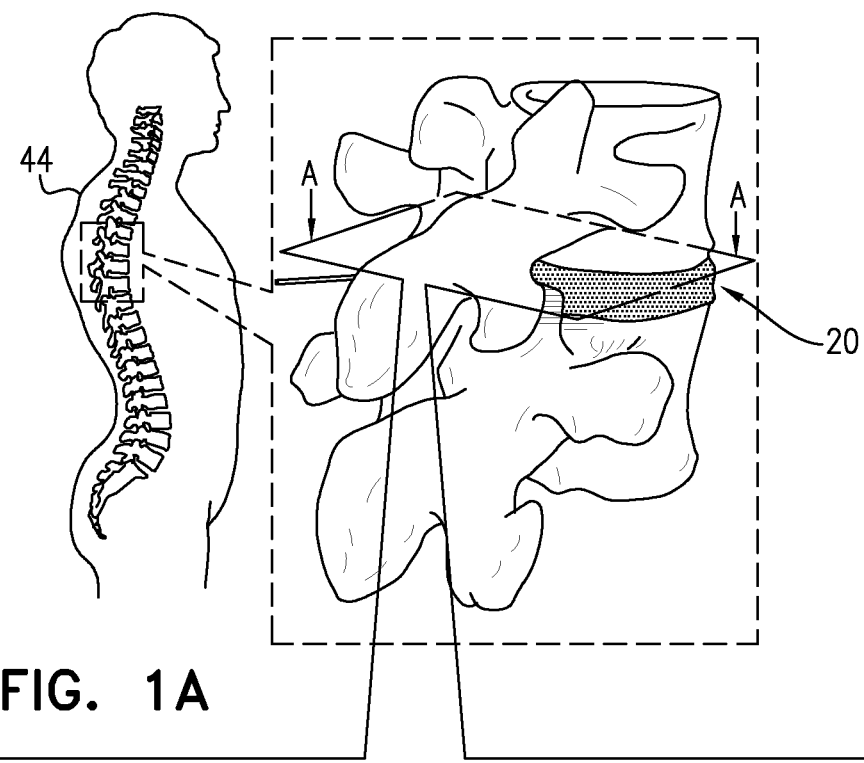
FIG. 1A
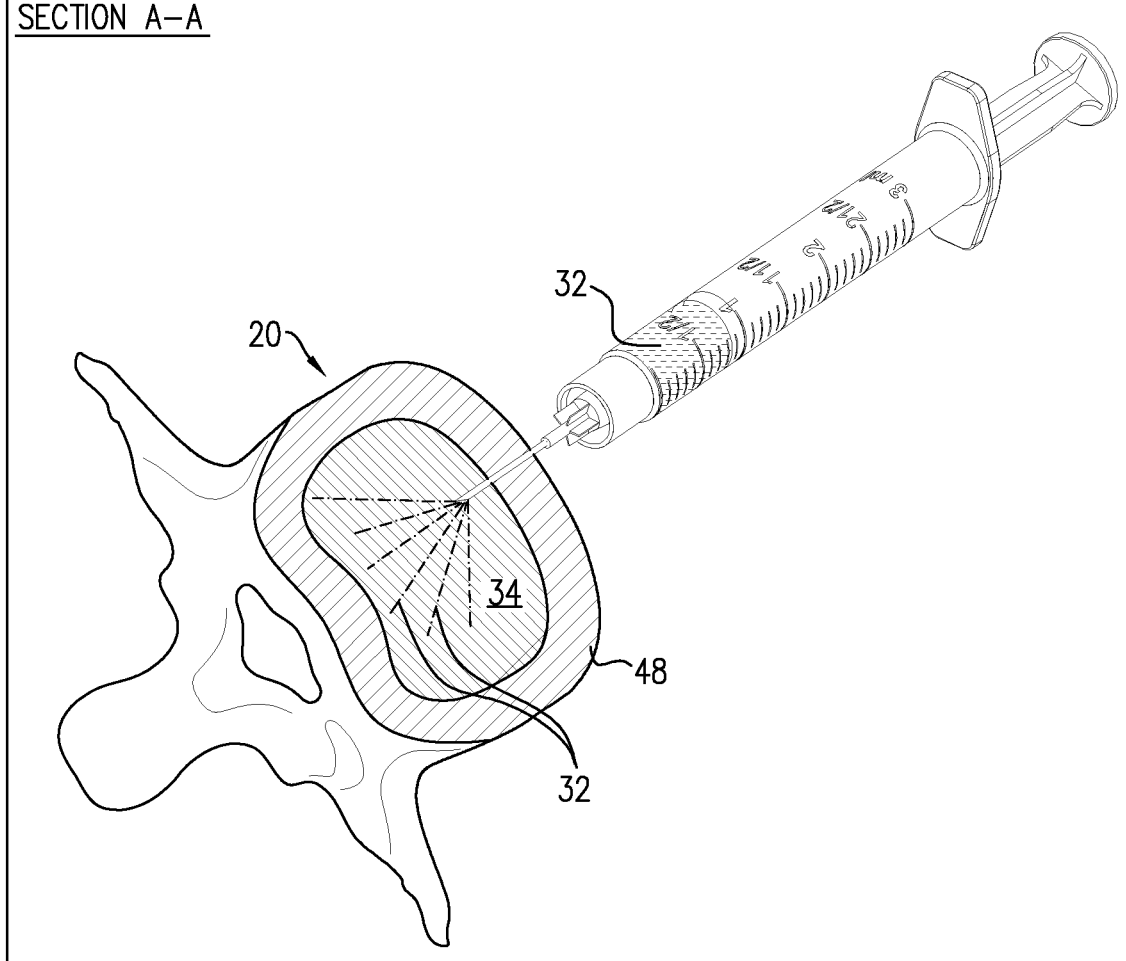
SECTION A-A

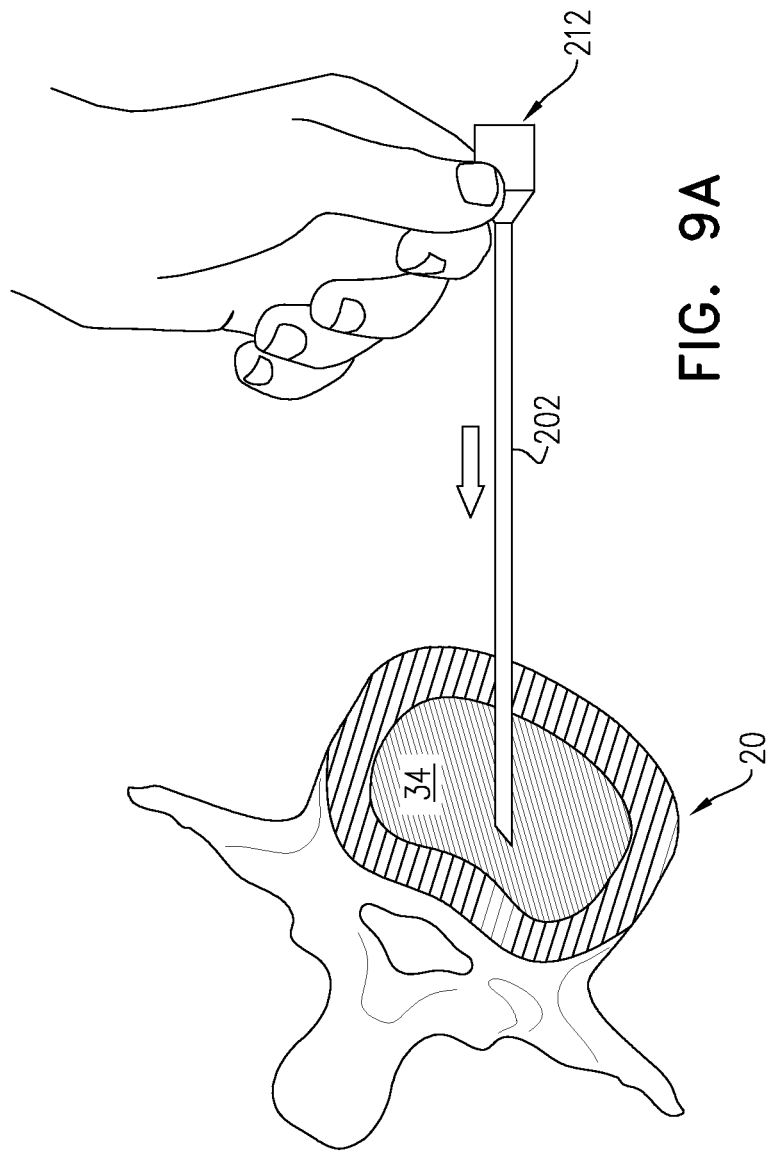

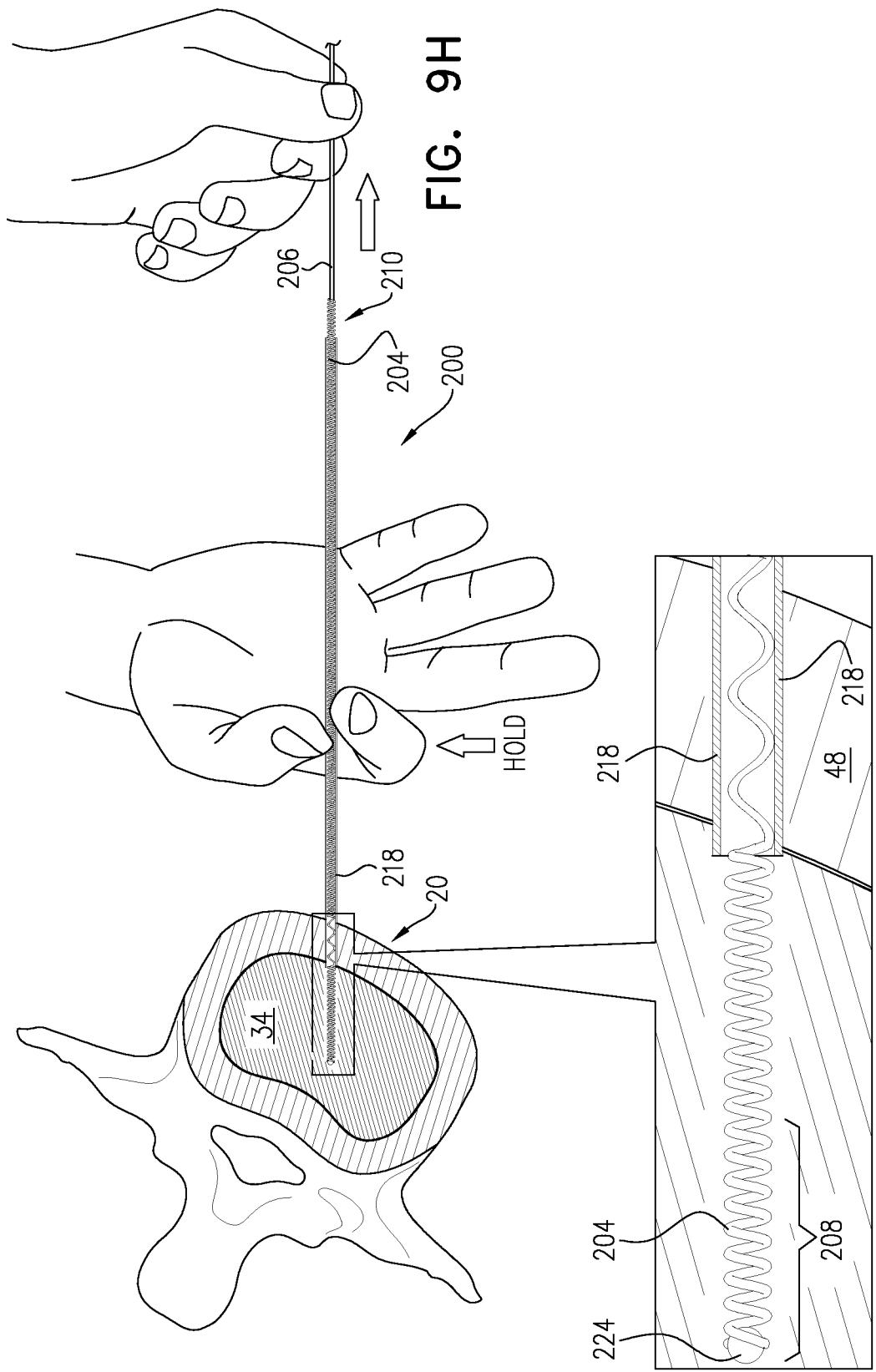

SYNERGISTIC THERAPIES FOR INTER VERTEBRAL DISC DEGENERATION

CROSS-REFERENCE TO RELATED APPLICATIONS

The present application is a continuation of U.S. application Ser. No. 17/306,209, filed May 3, 2021, now U.S. Pat. No. 11,298,530, which is incorporated herein by reference.

FIELD OF THE APPLICATION

The present invention relates generally to treatment of intervertebral disc degeneration.

BACKGROUND OF THE APPLICATION

The intervertebral discs form cartilaginous joints between the endplates of vertebrae to provide shock absorption. The discs include two main regions: the nucleus pulposus, which is an inner, soft and highly hydrated structure, and the annulus fibrosus, which is a strong structure including lamellae (concentric sheets of collagen fibers), which surrounds the nucleus. The three major constituents of the discs are water, fibrillar collagens, and aggrecan. The proportion of these components varies across the disc, with the nucleus having a higher concentration of aggrecan and water and a lower collagen content than other regions of the disc. The loss of water content, particularly in the nucleus pulposus, is associated with disc degeneration, and with a decrease in disc height and abnormal loading of other spinal structures.

U.S. Pat. No. 8,577,469 to Gross, which is assigned to the assignee of the present application and is incorporated herein by reference, describes apparatus for treating an intervertebral disc of a subject. The apparatus includes a first electrode, configured to be inserted into a nucleus pulposus of the disc, and a second electrode, configured to be placed outside of the nucleus pulposus, in a vicinity of the nucleus pulposus. A control unit is configured to drive a current between the first and second electrodes, and to configure the current to electroosmotically drive fluid between inside and outside the nucleus pulposus. Other embodiments are also described US Patent Application Publication 2005/0277996 to Podhajsky describes a method for reducing intervertebral pressure, including providing an electrode, having proximal and distal ends, and a generator, which is operatively connected to the proximal end of the electrode, and is configured to supply radiofrequency current thereto. The method also includes inserting at least a portion of the distal end of the electrode into the nucleus pulposus of an intervertebral disc and activating the generator to heat the nucleus pulposus. The electrode may be inserted into the intervertebral disc through its first lateral side and/or its second lateral side, and may be substantially parallel to the major or minor axis of the nucleus pulposus.

SUMMARY OF THE APPLICATION

Some embodiments of the present invention provide methods for combined therapy for the treatment of an intervertebral disc of a subject. The combination of cell therapy and/or growth factors with the restoration of the electrochemical osmotic properties of the disc provides the nutritional supply to regenerate the disc tissue and restore pumping-out of cytokines and pain markers. Some of the methods comprise delivering cells or a growth factor to a nucleus pulposus of the intervertebral disc, or administering gene therapy to nucleus pulposus cells. At least one intra-pulposus exposed electrode surface is implanted in the nucleus pulposus, and at least one extra-pulposus exposed electrode surface is implanted in a body of the subject outside the nucleus pulposus. The cells, growth factor, or gene therapy, as the case may be, are supported by activating control circuitry to drive the intra-pulposus and the extra-pulposus exposed electrode surfaces to electroosmotically drive nutrient-containing fluid into the nucleus pulposus. For some applications, the nutrient-containing fluid includes oxygen and/or glucose.

Other methods of the present invention comprise implanting at least one intra-pulposus exposed electrode surface in the nucleus pulposus, and the at least one extra-pulposus exposed electrode surface in the body of the subject outside the nucleus pulposus. Control circuitry is activated to drive the intra-pulposus and the extra-pulposus exposed electrode surfaces to electroosmotically drive fluid into the nucleus pulposus. Enzyme therapy is administered to the intervertebral disc or its surroundings so as to facilitate electroosmotically driving the fluid into the nucleus pulposus. Alternatively or additionally, supplemental fluid is delivered (e.g., injected) to the intervertebral disc (the nucleus pulposus or the annulus fibrosus) or into tissue surrounding the intervertebral disc.

Still other methods of the present invention comprise delivering (e.g., injecting), to the intervertebral disc (the nucleus pulposus or the annulus fibrosus) or into tissue surrounding the intervertebral disc, a biomaterial configured to treat degeneration of the intervertebral disc. Control circuitry is activated to drive the intra-pulposus and the extra-pulposus exposed electrode surfaces to electroosmotically drive fluid into the nucleus pulposus.

There is therefore provided, in accordance with an Inventive Concept 1 of the present invention, a method for treating an intervertebral disc of a subject, the method including:
delivering cells to a nucleus pulposus of the intervertebral disc;
implanting at least one intra-pulposus exposed electrode surface in the nucleus pulposus;
implanting at least one extra-pulposus exposed electrode surface in a body of the subject outside the nucleus pulposus; and
supporting the delivered cells by activating control circuitry to drive the intra-pulposus and the extra-pulposus exposed electrode surfaces to electroosmotically drive nutrient-containing fluid into the nucleus pulposus.

Inventive Concept 2. The method according to Inventive Concept 1, wherein delivering the cells to the nucleus pulposus includes injecting the cells into the nucleus pulposus.

Inventive Concept 3. The method according to Inventive Concept 1, wherein delivering the cells to the nucleus pulposus includes delivering the cells to the body of the subject outside the nucleus pulposus such that the cells migrate into the nucleus pulposus.

Inventive Concept 4. The method according to Inventive Concept 3, wherein delivering the cells to the body of the subject outside the nucleus pulposus includes delivering the cells to a vertebral endplate such that the cells migrate into the nucleus pulposus.

Inventive Concept 5. The method according to Inventive Concept 3, wherein delivering the cells to the nucleus pulposus includes delivering the cells to an annulus fibrosus of the intervertebral disc.

Inventive Concept 6. The method according to Inventive Concept 3, wherein delivering the cells to the nucleus pulposus includes, while at least some of the cells are outside the nucleus pulposus, activating the control circuitry to drive the intra-pulposus and the extra-pulposus exposed electrode surfaces to electroosmotically drive the cells into the nucleus pulposus.

Inventive Concept 7. The method according to Inventive Concept 1, wherein supporting the delivered cells includes supporting the delivered cells by activating the control circuitry to apply a mean voltage of less than 1.23V between the intra-pulposus exposed electrode surface and the extra-pulposus exposed electrode surface, so as not to cause electrolysis.

Inventive Concept 8. The method according to Inventive Concept 1, wherein activating the control circuitry includes activating the control circuitry to:

repeatedly assume an electroosmotic mode of operation in alternation with an oxygen-generating mode of operation, in the electroosmotic mode of operation, electroosmotically drive the nutrient-containing fluid into the nucleus pulposus, by applying a mean voltage of less than 1.23V between the intra-pulposus exposed electrode surface and the extra-pulposus exposed electrode surface, and in the oxygen-generating mode of operation, generate oxygen within the nucleus pulposus by electrolysis, by applying a mean voltage of at least 1.23V between the intra-pulposus exposed electrode surface and the extra-pulposus exposed electrode surface.

Inventive Concept 9. The method according to Inventive Concept 8, wherein activating the control circuitry includes activating the control circuitry to, during a period of time, assume (a) the electroosmotic mode of operation at least 10 times for an aggregate first duration and (b) the oxygen-generating mode of operation at least 10 times for an aggregate second duration that is less than 10% of the aggregate first duration.

Inventive Concept 10. The method according to Inventive Concept 9, wherein the aggregate second duration is less than 1% of the aggregate first duration.

Inventive Concept 11. The method according to Inventive Concept 1, wherein the nutrient-containing fluid includes oxygen, and wherein supporting the delivered cells includes supporting the delivered cells by activating the control circuitry to drive the intra-pulposus and the extra-pulposus exposed electrode surfaces to electroosmotically drive the oxygen-containing fluid into the nucleus pulposus.

Inventive Concept 12. The method according to Inventive Concept 1, wherein the nutrient-containing fluid includes glucose, and wherein supporting the delivered cells includes supporting the delivered cells by activating the control circuitry to drive the intra-pulposus and the extra-pulposus exposed electrode surfaces to electroosmotically drive the glucose-containing fluid into the nucleus pulposus.

Inventive Concept 13. The method according to Inventive Concept 1, wherein delivering the cells to the nucleus pulposus includes delivering stem cells to the nucleus pulposus.

Inventive Concept 14. The method according to Inventive Concept 1, wherein delivering the cells to the nucleus pulposus includes delivering disc cells to the nucleus pulposus.

Inventive Concept 15. The method according to Inventive Concept 1, wherein delivering the cells to the nucleus pulposus includes delivering notochordal cells to the nucleus pulposus.

Inventive Concept 16. The method according to Inventive Concept 1, wherein supporting the delivered cells includes supporting the delivered cells by activating the control circuitry to intermittently drive, during a plurality of sessions, the intra-pulposus and the extra-pulposus exposed electrode surfaces to electroosmotically drive the nutrient-containing fluid into the nucleus pulposus.

Inventive Concept 17. The method according to Inventive Concept 16, wherein an average duration of non-activation periods between sequential ones of the sessions is at least 12 hours.

Inventive Concept 18. The method according to Inventive Concept 16, wherein the plurality of sessions includes at least 10 sessions.

Inventive Concept 19. The method according to Inventive Concept 16, wherein supporting the delivered cells includes supporting the delivered cells by activating the control circuitry to intermittently drive the intra-pulposus and the extra-pulposus exposed electrode surfaces to electroosmotically drive the nutrient-containing fluid into the nucleus pulposus during one or more of the sessions during each 24-hour period.

Inventive Concept 20. The method according to Inventive Concept 19, wherein supporting the delivered cells includes supporting the delivered cells by activating the control circuitry to intermittently drive the intra-pulposus and the extra-pulposus exposed electrode surfaces to electroosmotically drive the nutrient-containing fluid into the nucleus pulposus during exactly one of the sessions during each 24-hour period.

Inventive Concept 21. The method according to Inventive Concept 16, wherein the plurality of sessions extends over at least one week.

Inventive Concept 22. The method according to Inventive Concept 1, wherein supporting the delivered cells includes supporting the delivered cells by activating the control circuitry to apply direct current between the intra-pulposus and the extra-pulposus exposed electrode surfaces.

Inventive Concept 23. The method according to Inventive Concept 1, further including delivering an enzyme to the intervertebral disc or tissue around the intervertebral disc so as to facilitate electroosmotically driving the nutrient-containing fluid into the nucleus pulposus.

There is therefore provided, in accordance with an Inventive Concept 24 of the present invention, a method for treating an intervertebral disc of a subject, the method including:

implanting at least one intra-pulposus exposed electrode surface in a nucleus pulposus of the intervertebral disc;

implanting at least one extra-pulposus exposed electrode surface in a body of the subject outside the nucleus pulposus;

delivering cells to the body of the subject outside the nucleus pulposus; and while at least some of the cells are outside the nucleus pulposus, activating control circuitry to drive the intra-pulposus and the extra-pulposus exposed electrode surfaces to electroosmotically drive the cells into the nucleus pulposus.

Inventive Concept 25. The method according to Inventive Concept 24, further including supporting the delivered cells by activating the control circuitry to drive the intra-pulposus and the extra-pulposus exposed electrode surfaces to electroosmotically drive nutrient-containing fluid into the nucleus pulposus.

Inventive Concept 26. The method according to Inventive Concept 24, wherein delivering the cells to the body of the subject outside the nucleus pulposus includes delivering the cells to a vertebral endplate.

Inventive Concept 27. The method according to Inventive Concept 24, wherein delivering the cells to the body of the subject outside the nucleus pulposus includes delivering the cells to an annulus fibrosus of the intervertebral disc.

There is therefore provided, in accordance with an Inventive Concept 28 of the present invention, a method for treating an intervertebral disc of a subject, the method including:

administering gene therapy to nucleus pulposus cells of a nucleus pulposus of the intervertebral disc;

implanting at least one intra-pulposus exposed electrode surface in the nucleus pulposus;

implanting at least one extra-pulposus exposed electrode surface in a body of the subject outside the nucleus pulposus; and supporting the gene therapy by activating control circuitry to drive the intra-pulposus and the extra-pulposus exposed electrode surfaces to electroosmotically drive nutrient-containing fluid into the nucleus pulposus.

Inventive Concept 29. The method according to Inventive Concept 28, wherein supporting the gene therapy includes supporting the gene therapy by activating the control circuitry to apply a mean voltage of less than 1.23V between the intra-pulposus exposed electrode surface and the extra-pulposus exposed electrode surface, so as not to cause electrolysis.

There is therefore provided, in accordance with an Inventive Concept 30 of the present invention, a method for treating an intervertebral disc of a subject, the method including:

delivering a growth factor to a nucleus pulposus of the intervertebral disc;

implanting at least one intra-pulposus exposed electrode surface in the nucleus pulposus;

implanting at least one extra-pulposus exposed electrode surface in a body of the subject outside the nucleus pulposus; and supporting the growth factor by activating control circuitry to drive the intra-pulposus and the extra-pulposus exposed electrode surfaces to electroosmotically drive nutrient-containing fluid into the nucleus pulposus.

Inventive Concept 31. The method according to Inventive Concept 30, wherein delivering the growth factor to the nucleus pulposus includes injecting the growth factor into the nucleus pulposus.

Inventive Concept 32. The method according to Inventive Concept 30, wherein delivering the growth factor to the nucleus pulposus includes delivering the growth factor to the body of the subject outside the nucleus pulposus such that the growth factor moves into the nucleus pulposus.

Inventive Concept 33. The method according to Inventive Concept 32, wherein delivering the growth factor to the body of the subject outside the nucleus pulposus includes delivering the growth factor to a vertebral endplate such that the growth factor moves into the nucleus pulposus.

Inventive Concept 34. The method according to Inventive Concept 32, wherein delivering the growth factor to the body of the subject outside the nucleus pulposus includes delivering the growth factor to an annulus fibrosus of the intervertebral disc such that the growth factor moves into the nucleus pulposus.

Inventive Concept 35. The method according to Inventive Concept 32, wherein delivering the growth factor to the nucleus pulposus includes, while at least some of the growth factor is outside the nucleus pulposus, activating the control circuitry to drive the intra-pulposus and the extra-pulposus exposed electrode surfaces to electroosmotically drive the growth factor into the nucleus pulposus.

Inventive Concept 36. The method according to Inventive Concept 30, wherein supporting the growth factor includes supporting the growth factor by activating the control circuitry to apply a mean voltage of less than 1.23V between the intra-pulposus exposed electrode surface and the extra-pulposus exposed electrode surface, so as not to cause electrolysis.

There is therefore provided, in accordance with an Inventive Concept 37 of the present invention, a method for treating an intervertebral disc of a subject, the method including:

implanting at least one intra-pulposus exposed electrode surface in a nucleus pulposus of the intervertebral disc;

implanting at least one extra-pulposus exposed electrode surface in a body of the subject outside the nucleus pulposus;

delivering a growth factor to the body of the subject outside the nucleus pulposus; and while at least some of the growth factor is outside the nucleus pulposus, activating control circuitry to drive the intra-pulposus and the extra-pulposus exposed electrode surfaces to electroosmotically drive the growth factor into the nucleus pulposus.

Inventive Concept 38. The method according to Inventive Concept 37, further including supporting the growth factor by activating control circuitry to drive the intra-pulposus and the extra-pulposus exposed electrode surfaces to electroosmotically drive nutrient-containing fluid into the nucleus pulposus.

Inventive Concept 39. The method according to Inventive Concept 37, wherein delivering the growth factor to the body of the subject outside the nucleus pulposus includes delivering the growth factor to a vertebral endplate.

Inventive Concept 40. The method according to Inventive Concept 37, wherein delivering the growth factor to the body of the subject outside the nucleus pulposus includes delivering the growth factor to an annulus fibrosus of the intervertebral disc.

There is therefore provided, in accordance with an Inventive Concept 41 of the present invention, a method for treating an intervertebral disc of a subject, the method including:

implanting at least one intra-pulposus exposed electrode surface in a nucleus pulposus of the intervertebral disc;

implanting at least one extra-pulposus exposed electrode surface in a body of the subject outside the nucleus pulposus;

activating control circuitry to drive the intra-pulposus and the extra-pulposus exposed electrode surfaces to electroosmotically drive fluid into the nucleus pulposus; and delivering an enzyme to the intervertebral disc or tissue around the intervertebral disc so as to facilitate electroosmotically driving the fluid into the nucleus pulposus.

Inventive Concept 42. The method according to Inventive Concept 41, wherein activating the control circuitry includes activating the control circuitry to apply a mean voltage of less than 1.23V between the intra-pulposus exposed electrode surface and the extra-pulposus exposed electrode surface, so as not to cause electrolysis.

There is therefore provided, in accordance with an Inventive Concept 43 of the present invention, a method for treating an intervertebral disc of a subject, the method including:

implanting at least one intra-pulposus exposed electrode surface in a nucleus pulposus of the intervertebral disc;

implanting at least one extra-pulposus exposed electrode surface in a body of the subject outside the nucleus pulposus;

administering an enzyme to the body of the subject outside the nucleus pulposus; and while at least some of the enzyme outside is the nucleus pulposus, activating control circuitry to drive the intra-pulposus and the extra-pulposus exposed electrode surfaces to electroosmotically drive the enzyme into the nucleus pulposus.

There is therefore provided, in accordance with an Inventive Concept 44 of the present invention, a method for treating an intervertebral disc of a subject, the method including:

implanting at least one intra-pulposus exposed electrode surface in a nucleus pulposus of the intervertebral disc;

implanting at least one extra-pulposus exposed electrode surface in a body of the subject outside the nucleus pulposus;

activating control circuitry to drive the intra-pulposus and the extra-pulposus exposed electrode surfaces to electroosmotically drive bodily fluid from the body of the subject into the nucleus pulposus; and delivering supplemental fluid to the intervertebral disc or tissue surrounding the intervertebral disc.

Inventive Concept 45. The method according to Inventive Concept 44, wherein delivering the supplemental fluid includes delivering saline solution to the intervertebral disc or tissue surrounding the intervertebral disc.

Inventive Concept 46. The method according to Inventive Concept 44, wherein delivering the supplemental fluid includes delivering a nutrient-containing fluid to the intervertebral disc or tissue surrounding the intervertebral disc.

Inventive Concept 47. The method according to Inventive Concept 44, wherein delivering the supplemental fluid includes intermittently delivering, during a plurality of delivery sessions, the supplemental fluid to the intervertebral disc or tissue surrounding the intervertebral disc, and wherein activating the control circuitry includes activating the control circuitry to intermittently drive, during a plurality of driving sessions, the intra-pulposus and the extra-pulposus exposed electrode surfaces to electroosmotically drive the supplemental fluid into the nucleus pulposus.

Inventive Concept 48. The method according to Inventive Concept 44, wherein delivering the supplemental fluid includes delivering the supplemental fluid from a reservoir implanted in the body of the subject.

There is therefore provided, in accordance with an Inventive Concept 49 of the present invention, a method for treating degeneration of an intervertebral disc of a subject, the method including:

delivering, to the intervertebral disc or tissue around the intervertebral disc, a biomaterial configured to treat the degeneration;

implanting at least one intra-pulposus exposed electrode surface in a nucleus pulposus of the intervertebral disc;

implanting at least one extra-pulposus exposed electrode surface in a body of the subject outside the nucleus pulposus; and activating control circuitry to drive the intra-pulposus and the extra-pulposus exposed electrode surfaces to electroosmotically drive fluid into the nucleus pulposus.

Inventive Concept 50. The method according to Inventive Concept 49, wherein the biomaterial includes a gel.

Inventive Concept 51. The method according to Inventive Concept 49, wherein the biomaterial includes a structural filler.

Inventive Concept 52. The method according to Inventive Concept 49, wherein the biomaterial includes a matrix.

Inventive Concept 53. The method according to Inventive Concept 49, wherein the biomaterial includes a polymer.

Inventive Concept 54. The method according to Inventive Concept 49, wherein the biomaterial includes hyaluronic acid.

Inventive Concept 55. The method according to Inventive Concept 49, wherein delivering the biomaterial to the nucleus pulposus includes delivering the biomaterial to the tissue around the intervertebral disc such that the biomaterial moves into the nucleus pulposus.

Inventive Concept 56. The method according to Inventive Concept 55, wherein delivering the biomaterial to the tissue around the intervertebral disc includes delivering the biomaterial to a vertebral endplate such that the biomaterial moves into the nucleus pulposus.

Inventive Concept 57. The method according to Inventive Concept 55, wherein delivering the biomaterial to the tissue around the intervertebral disc includes delivering the biomaterial to an annulus fibrosus of the intervertebral disc such that the biomaterial moves into the nucleus pulposus.

Inventive Concept 58. The method according to Inventive Concept 55, wherein delivering the biomaterial to the nucleus pulposus includes, while at least some of the biomaterial is outside the nucleus pulposus, activating the control circuitry to drive the intra-pulposus and the extra-pulposus exposed electrode surfaces to electroosmotically drive the biomaterial into the nucleus pulposus.

There is therefore provided, in accordance with an Inventive Concept 59 of the present invention, a method for treating degeneration of an intervertebral disc of a subject, the method including:

implanting at least one intra-pulposus exposed electrode surface in a nucleus pulposus of the intervertebral disc;

implanting at least one extra-pulposus exposed electrode surface in a body of the subject outside the nucleus pulposus;

delivering, to the body of the subject outside the nucleus pulposus, a biomaterial configured to treat the degeneration;

while at least some of the biomaterial is outside the nucleus pulposus, activating control circuitry to drive the intra-pulposus and the extra-pulposus exposed electrode surfaces to electroosmotically drive the biomaterial into the nucleus pulposus.

There is therefore provided, in accordance with an Inventive Concept 60 of the present invention, a method for implanting an electrode, the method including:

inserting a needle into tissue of a body of a subject such that (a) a distal longitudinal portion of the needle, including a distal end of the needle, is positioned within a nucleus pulposus of an intervertebral disc of the subject, and (b) a proximal portion of the needle, including a proximal end opening of the needle, remain outside the subject's body;

distally advancing the electrode into the needle while a stylet is disposed within a longitudinal channel defined by a coiled wire of the electrode;

distally advancing the electrode and the stylet together through the needle until a distal non-electrically-insulated longitudinal segment of the coiled wire of the electrode is positioned within the nucleus pulposus, and the stylet, the needle, and the coiled wire remain partially outside the subject's body, with the stylet and the coiled wire extending proximally out of a proximal end of the needle;

thereafter, while holding the stylet axially stationary with respect to the nucleus pulposus, proximally withdrawing the needle from the subject's body, leaving the distal non-electrically-insulated longitudinal segment of the coiled wire within the nucleus pulposus, with a distal end of the stylet within the longitudinal channel of the coiled wire, including within the distal non-electrically-insulated longitudinal segment; and proximally withdrawing the stylet from the subject's body and from the longitudinal channel of the coiled wire, while leaving the distal non-electrically-insulated longitudinal segment of the coiled wire within the nucleus pulposus.

Inventive Concept 61. The method according to Inventive Concept 60, wherein distally advancing the needle through the tissue into the nucleus pulposus includes distally advancing the needle through the tissue into the nucleus pulposus while the distal non-electrically-insulated longitudinal segment of the coiled wire is constrained only by the needle and the stylet.

Inventive Concept 62. The method according to Inventive Concept 60, wherein the electrode further includes a tubular insulator in which the coiled wire is partially disposed, with the distal non-electrically-insulated longitudinal segment of the coiled wire extending distally out of a distal end of the tubular insulator, and wherein proximally withdrawing the needle includes proximally withdrawing the needle while leaving (a) the distal non-electrically-insulated longitudinal segment of the coiled wire within the nucleus pulposus, and (b) the tubular insulator at least partially within the subject's body, at least partially outside the nucleus pulposus.

Inventive Concept 63. The method according to Inventive Concept 62, wherein proximally withdrawing the needle includes proximally withdrawing the needle while leaving the tubular insulator at least partially within an annulus fibrosus of the intervertebral disc.

Inventive Concept 64. The method according to Inventive Concept 60, further including driving the electrode to apply a current to the nucleus pulposus.

Inventive Concept 65. The method according to Inventive Concept 60, wherein the stylet is coated with a friction-reducing coating.

Inventive Concept 66. The method according to Inventive Concept 60, wherein the needle includes a plurality of radiopaque markers, and wherein distally advancing the needle through the tissue into the nucleus pulposus includes observing the radiopaque markers to confirm that the distal longitudinal portion of the needle is disposed in the nucleus pulposus.

Inventive Concept 67. The method according to Inventive Concept 66, wherein the plurality of radiopaque markers are arranged as a ruler along the needle.

Inventive Concept 68. The method according to Inventive Concept 60, wherein the electrode includes a distal-most non-coiled tip, which is disposed at a distal end of the coiled wire, and which is shaped so as to define a proximally-facing surface.

Inventive Concept 69. The method according to Inventive Concept 68, wherein the distal-most non-coiled tip is shaped so as to define an atraumatic distally-facing end surface.

Inventive Concept 70. The method according to Inventive Concept 69, wherein the atraumatic distally-facing end surface is spherical.

Inventive Concept 71. The method according to Inventive Concept 68, wherein the distal-most non-coiled tip is electrically conductive and is coupled in electrical communication with the coiled wire.

The present invention will be more fully understood from the following detailed description of embodiments thereof, taken together with the drawings, in which:

BRIEF DESCRIPTION OF THE DRAWINGS

FIGS. 1A-B are schematic illustrations of a method for treating an intervertebral disc of a subject, in accordance with some applications of the present invention;

FIGS. 9A-J are schematic illustrations of a method for implanting an electrode in a nucleus pulposus, in accordance with an application of the present invention.

DETAILED DESCRIPTION OF APPLICATIONS

Figure 1B:
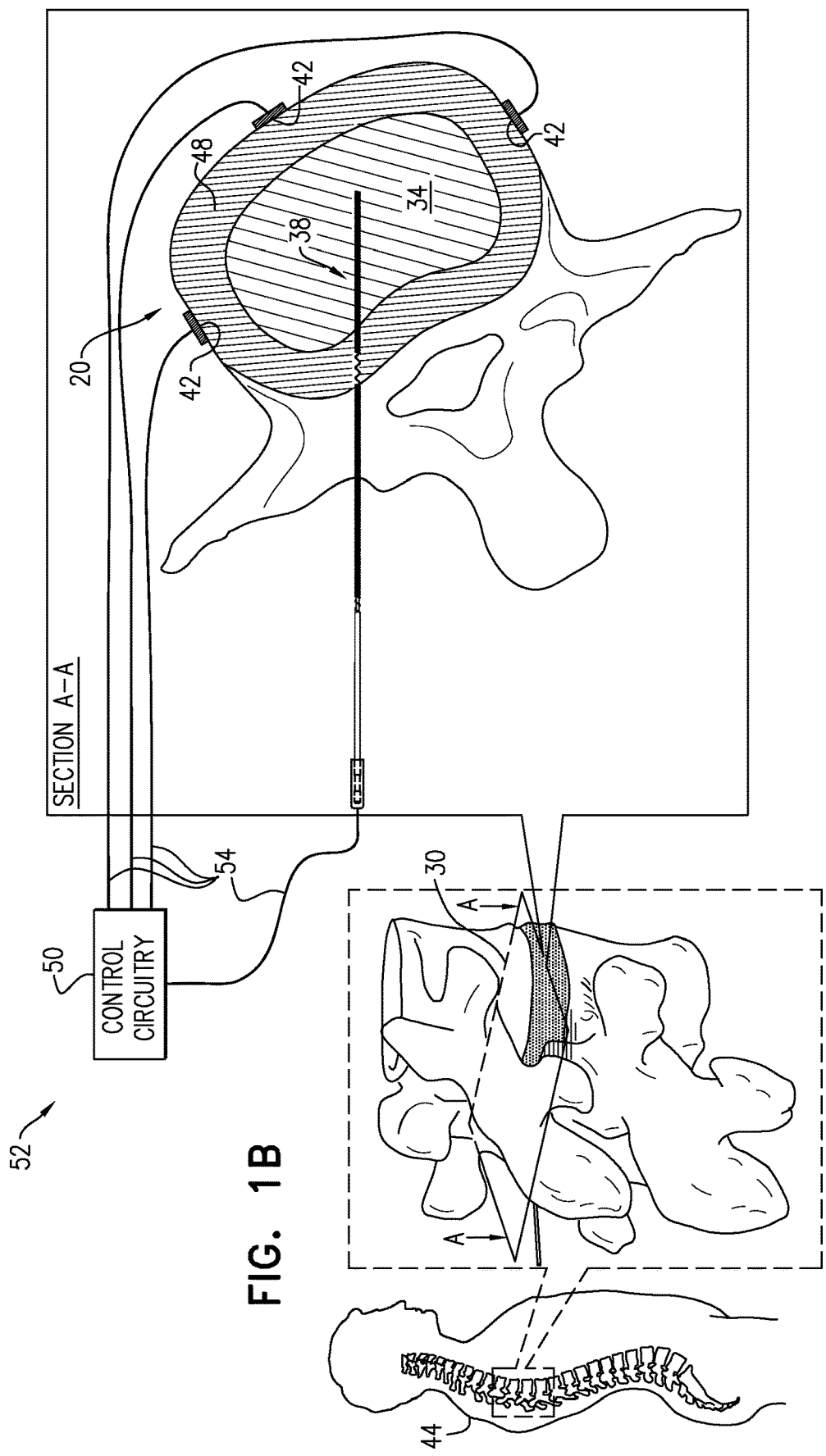

FIGS. 1A-B are schematic illustrations of a method for treating an intervertebral disc 20 of a subject, in accordance with some applications of the present invention.

Figure 2:
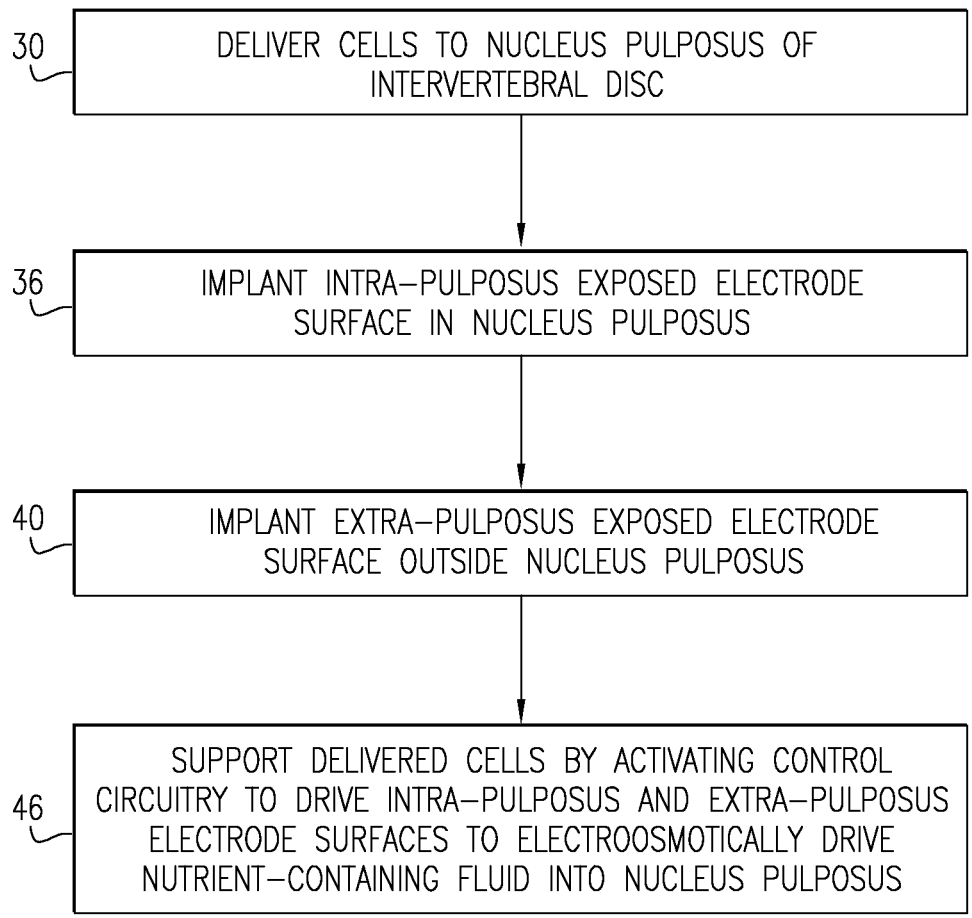
FIG. 2 is a flowchart schematically illustrating the method of FIGS. 1A-B, in accordance with some applications of the present invention.

FIG. 2 is a flowchart schematically illustrating the method of FIGS. 1A-B, in accordance with some applications of the present invention.

At a cell delivery step 30 of the method, cells 32 are delivered to a nucleus pulposus 34 of intervertebral disc 20, such as shown in FIG. 1A. By way of example, cells 32 are shown being injected into nucleus pulposus 34 via an annulus fibrosus 48 of disc 20. Cells 32 may alternatively or additionally be delivered to nucleus pulposus 34 in other ways, such as into a vertebral endplate, into nucleus pulposus 34 via a vertebral endplate, and/or to the body of the subject outside the nucleus pulposus (typically to tissue around intervertebral disc 20), which may be less invasive;

when delivered in these other ways, cells 32 migrate into nucleus pulposus 34, optionally because of the electroosmotically driving of fluid into nucleus pulposus 34 by activation of control circuitry 50 to drive intra-pulposus and extra-pulposus exposed electrode surfaces 38 and 42, such as described herein. Alternatively, cells 32 may be delivered into an annulus fibrosus 48, in which case cells 32 may optionally migrate into nucleus pulposus 34 by activation of control circuitry 50 to drive intra-pulposus and extra-pulposus exposed electrode surfaces 38 and 42, such as described herein. All of the ways of delivery cells 32 may optionally be performed, for example, by injecting or by releasing (e.g., slow-releasing) the cells from a container, such as an implanted container.

Figure 8:
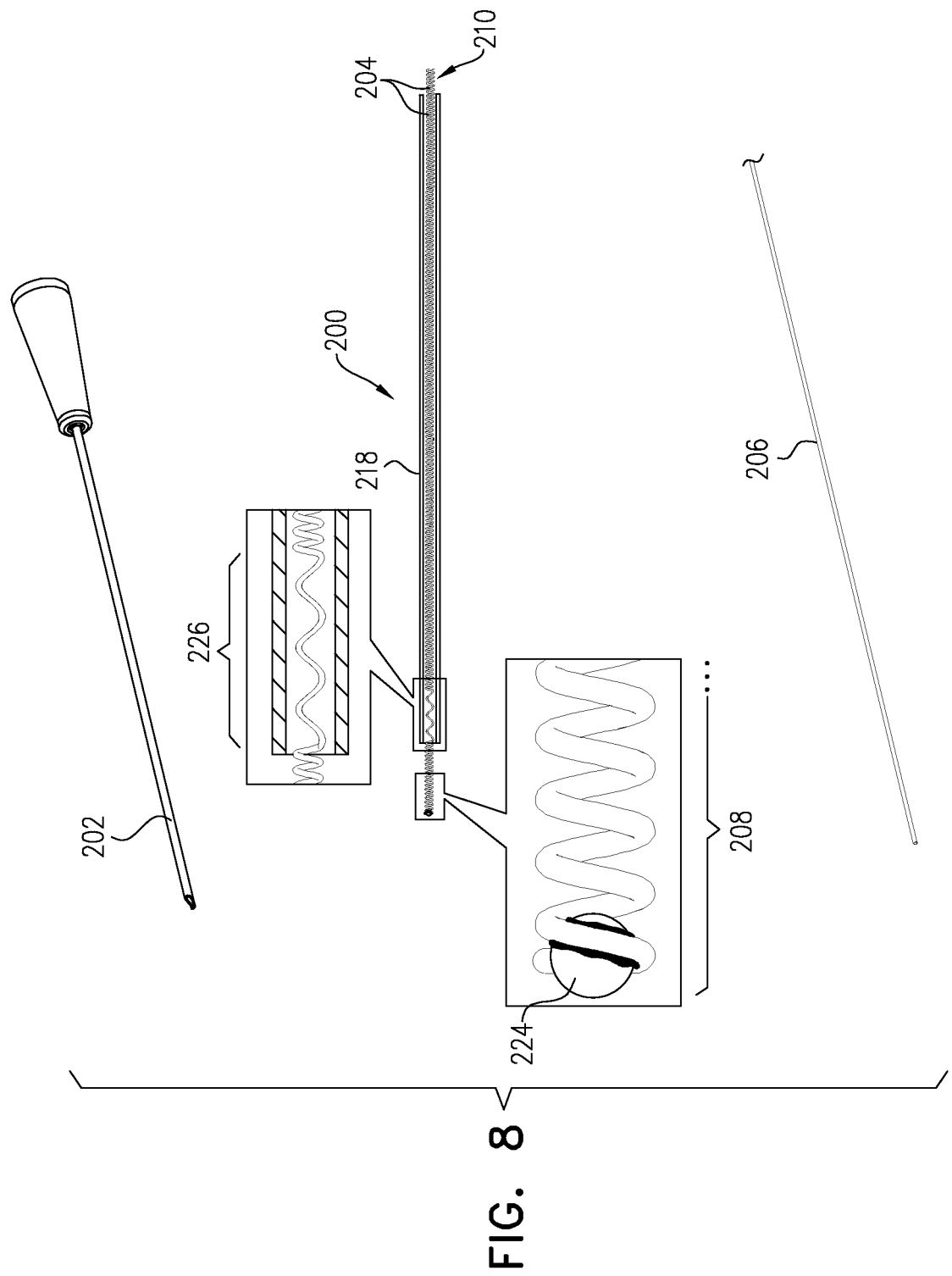
FIG. 8 is a schematic illustration of a kit, in accordance with an application of the present invention.

At an intra-pulposus electrode implantation step 36, at least one intra-pulposus exposed electrode surface 38 (which is electrically conductive) is implanted (typically chronically) in nucleus pulposus 34, such as shown in FIG. 1B. Optionally, techniques described hereinbelow with reference to FIG. 8 and/or FIGS. 9A-J are used to implant the at least one intra-pulposus exposed electrode surface 38.

At an extra-pulposus electrode implantation step 40, at least one extra-pulposus exposed electrode surface 42 (which is electrically conductive) is implanted (typically chronically) in a body 44 of the subject outside nucleus pulposus 34, such as shown in FIG. 1B. For example, extra-pulposus exposed electrode surface 42 may be implanted in a vicinity of an external surface of annulus fibrosus 48 of disc 20, either in physical contact with the external surface or not in physical contact with the external surface.

Alternatively, the at least one extra-pulposus exposed electrode surface 42 is placed outside body 44 of the subject, such as on an external surface of the skin (configuration not shown).

For some applications, a plurality of extra-pulposus exposed electrode surfaces 42 (e.g., at least 3, no more than 10, and/or between 3 and 10, such as exactly 3) are implanted (typically chronically) in body 44 outside nucleus pulposus 34, or are placed outside body 44.

For some applications, cells 32 include one or more of the following types of cells: autologous or allogenic stem cells (e.g., mesenchymal stem cells (MSCs)), disc cells (e.g., allogeneic disc cells), notochordal cells, allogeneic chondrocytes, and/or dermal fibroblast cells. For example, the MSCs may be derived from bone marrow aspirate or from adipose tissue, and/or may include autologous MSCs cultured in normal or hypoxic conditions.

At a cell support step 46, delivered cells 32 are supported by activating control circuitry 50 to drive intra-pulposus and extra-pulposus exposed electrode surfaces 38 and 42 to electroosmotically drive nutrient-containing fluid into nucleus pulposus 34.

Small nutrients such as oxygen and glucose are supplied to the disc's cells virtually entirely by diffusion; convective transport, arising from load-induced fluid movement in and out of the disc, has virtually no direct influence on transport of these nutrients. Consequently, there are steep concentration gradients of oxygen, glucose, and lactic acid across the disc; oxygen and glucose concentrations are lowest in the center of the nucleus where lactic acid concentrations are greatest. The actual levels of concentration depend on the balance between diffusive transport and cellular demand and can fall to critical levels if the endplate calcifies or nutritional demand increases.

As used in the present application, including in the claims, a "nutrient" is a substance used by cells within nucleus pulposus 34, including, for example, delivered cells 32, to survive and reproduce. As used in the present application, including in the claims, oxygen is considered a nutrient, because oxygen is essential for the survival and reproduction of cells.

For some applications, the nutrient-containing fluid includes oxygen, and, at cell support step 46, delivered cells 32 are supported by activating control circuitry 50 to drive intra-pulposus and extra-pulposus exposed electrode surfaces 38 and 42 to electroosmotically drive the oxygen-containing fluid into nucleus pulposus 34.

Alternatively or additionally, for some applications, the nutrient-containing fluid includes glucose, and, at cell support step 46, delivered cells 32 are supported by activating control circuitry 50 to drive intra-pulposus and extra-pulposus exposed electrode surfaces 38 and 42 to electroosmotically drive the glucose-containing fluid into nucleus pulposus 34.

Intra-pulposus electrode implantation step 36 may be performed before, after, or simultaneously with extra-pulposus electrode implantation step 40.

Intra-pulposus electrode implantation step 36 and extra-pulposus electrode implantation step 40 may be performed before or after cell delivery step 30. Alternatively, one of intra-pulposus electrode implantation step 36 and extra-pulposus electrode implantation step 40 may be performed before cell delivery step 30, and the other implantation step may be performed after cell delivery step 30. If intra-pulposus electrode implantation step 36 is performed before cell delivery step 30, cell delivery step 30 may optionally be performed using connector 300, described hereinbelow with reference to FIG. 10.

Optionally, an additional cell delivery step 30 is performed after cell support step 46, such as months or years after cell support step 46, such as if cells 32 need to be replaced or supplemented. This additional cell delivery step 30 may optionally be performed using connector 300, described hereinbelow with reference to FIG. 10.

For some applications, at cell support step 46, delivered cells 32 are supported by activating control circuitry 50 to apply a mean voltage of less than 1.23V between intra-pulposus exposed electrode surface 38 and extra-pulposus exposed electrode surface 42, so as not to cause electrolysis. For example, the mean voltage may be less than 1V, such as less than 500 mV, e.g., less than 300 mV.

For some applications, at cell support step 46, delivered cells 32 are supported by activating control circuitry 50 to apply direct current between intra-pulposus and extra-pulposus exposed electrode surfaces 38 and 42. For some applications, control circuitry 50 is activated to apply the direct current during alternating "on" and "off" periods; for example, the "on" periods may have an average duration of up to 1800 seconds, and the "off" periods may have an average duration of up to 300 seconds. For some applications, control circuitry 50 is activated to apply the direct current with an average amplitude of between 100 nA and 5 mA, such as between 1 and 5 mA. For some applications, the control unit is configured to apply the direct current as a series of pulses. For some applications, the control unit is configured to apply the direct current as the series of pulses with a duty cycle of between 20% and 95%.

For some applications, control circuitry 50 is activated to apply a voltage of between 0.6-2V, such as between 0.6 and 1.23V, between intra-pulposus and extra-pulposus exposed electrode surfaces 38 and 42.

Typically, control circuitry 50 is not configured to actively balance the applied positive and negative charges. Rather, control circuitry 50 is configured to allow the passive balancing of the applied positive and negative charges.

For some applications, control circuitry 50 is activated to drive intra-pulposus and extra-pulposus exposed electrode surfaces 38 and 42 for a total duration of between 6 and 24 hours per day.

For some applications, the method further comprises delivering an enzyme to intervertebral disc 20 or tissue around intervertebral disc 20 so as to facilitate electroosmotically driving the nutrient-containing fluid into nucleus pulposus 34.

This delivery may be performed using the techniques described hereinbelow with reference to FIG. 5.

Reference is made to FIG. 1B. Typically, intra-pulposus and extra-pulposus exposed electrode surfaces 38 and 42 and control circuitry 50 are elements of an intervertebral-disc-treatment system 52. Control circuitry 50 is typically electrically coupled, by one or more electrode leads 54, to intra-pulposus and extra-pulposus exposed electrode surfaces 38 and 42.

Optionally, intra-pulposus extra-pulposus exposed electrode surface 38, extra-pulposus exposed electrode surface 42, and/or control circuitry 50 may implement any of the techniques described in WO 2018/051338 to Gross et al., which is incorporated herein by reference.

Reference is again made to FIGS. 1A-B and 2. Typically, a healthcare worker, such as a physician, activates control circuitry 50 to provide the functions described herein. Activating the control circuitry may include configuring parameters and/or functions of the control circuitry (such as using a separate programmer or external controller), or activating the control circuitry to perform functions pre-programmed in the control circuitry. Control circuitry 50 typically comprises appropriate memory, processor(s), and hardware running software that is configured to provide the functionality of the control circuitry described herein.

Reference is still made to FIGS. 1A-B and 2. For some applications, control circuitry 50 is activated to:
 repeatedly assume an electroosmotic mode of operation in alternation with an oxygen-generating mode of operation,
 in the electroosmotic mode of operation, electroosmotically drive the nutrient-containing fluid into nucleus pulposus 34, by applying a mean voltage of less than 1.23V between intra-pulposus exposed electrode surface 38 and extra-pulposus exposed electrode surface 42 (such as by configuring intra-pulposus exposed electrode surface 38 to be a cathode, and extra-pulposus exposed electrode surface 42 to be an anode), and
 in the oxygen-generating mode of operation, generate oxygen within nucleus pulposus 34 by electrolysis, by applying a mean voltage of at least 1.23V (e.g., between 1.23V and 1.5V, and typically no more than 2V), between intra-pulposus exposed electrode surface 38 and the extra-pulposus exposed electrode surface 42 (such as by configuring intra-pulposus exposed electrode surface 38 to be an anode, and extra-pulposus exposed electrode surface 42 to be a cathode).

For some of these applications, control circuitry 50 is activated to, during a period of time, assume (a) the electroosmotic mode of operation at least 10 times for an aggregate first duration and (b) the oxygen-generating mode of operation at least 10 times for an aggregate second duration that is less than 10% of the aggregate first duration, such as less than 1% of the aggregate first duration.

Reference is still made to FIGS. 1A-B and 2. For some applications, delivered cells 32 are supported by activating control circuitry 50 to intermittently drive, during a plurality of sessions, intra-pulposus and extra-pulposus exposed electrode surfaces 38 and 42 to electroosmotically drive the nutrient-containing fluid into nucleus pulposus 34.

For some of these applications:
 an average duration of non-activation periods between sequential ones of the sessions is at least 12 hours,
 the plurality of sessions includes at least 10 sessions,
 the plurality of sessions extends over at least one week, such as over at least one month, and/or
 at least one the plurality of sessions commences at least one week (such as at least one month) after another one of the plurality of sessions commences.

For some of these applications, delivered cells 32 are supported by activating control circuitry 50 to intermittently drive intra-pulposus and extra-pulposus exposed electrode surfaces 38 and 42 to electroosmotically drive the nutrient-containing fluid into nucleus pulposus 34 during one or more of the sessions (e.g., during exactly one of the sessions) during each 24-hour period. For example, the one or more of the sessions (e.g., the exactly one of the sessions) may be at night, such as during sleep of the subject at night.

For some of these applications, delivered cells 32 are supported by activating control circuitry 50 to drive intra-pulposus and extra-pulposus exposed electrode surfaces 38 and 42 to electroosmotically drive the nutrient-containing fluid into nucleus pulposus 34 based on a circadian cycle of the subject.

Figure 3:
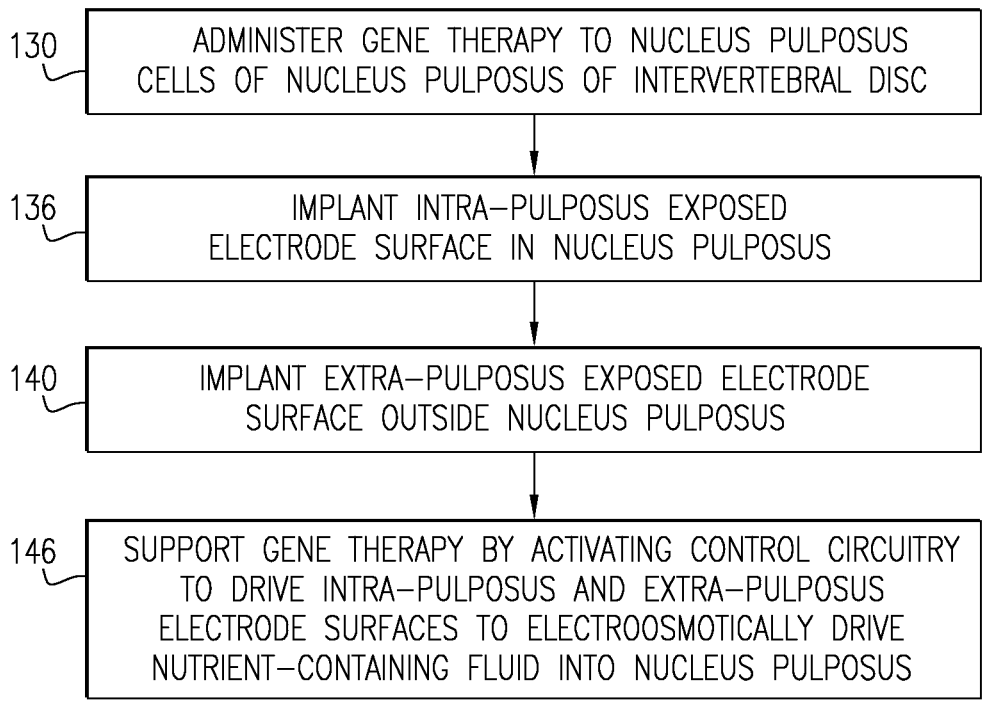
FIG. 3 is a flowchart schematically illustrating another method for treating an intervertebral disc, in accordance with some applications of the present invention.

Reference is again made to FIGS. 1A-B, and is additionally made to FIG. 3, which is a flowchart schematically illustrating a method for treating intervertebral disc 20, in accordance with some applications of the present invention. The method of FIG. 3 may be practiced in combination with any of the techniques described hereinabove for the method of FIG. 2, mutatis mutandis.

At a gene therapy administration step 130 of the method, gene therapy is administered to nucleus pulposus cells of nucleus pulposus 34 of intervertebral disc 20. For example, the therapeutic gene (e.g., in saline solution), or a biological construct encoding the therapeutic gene (e.g., in saline solution), may be delivered to nucleus pulposus 34, such as described hereinabove with reference to FIG. 1A regarding cells 32 at cell delivery step 30 of the method of FIG. 2, mutatis mutandis.

At an intra-pulposus electrode implantation step 136, at least one intra-pulposus exposed electrode surface 38 is implanted (typically chronically) in nucleus pulposus 34, such as shown in FIG. 1B.

At an extra-pulposus electrode implantation step 140, at least one extra-pulposus exposed electrode surface 42 is implanted (typically chronically) in body 44 of the subject outside nucleus pulposus 34, as shown in FIG. 1B. For example, extra-pulposus exposed electrode surface 42 may be implanted in a vicinity of an external surface of annulus fibrosus 48 of disc 20, either in physical contact with the external surface or not in physical contact with the external surface.

Alternatively, the at least one extra-pulposus exposed electrode surface 42 is placed outside body 44 of the subject, such as on an external surface of the skin (configuration not shown).

For some applications, the gene therapy includes one or more of the following types of gene therapy:
 virus-mediated (e.g., using a retrovirus, an adenovirus, an adeno-associated virus, a baculovirus, a lentivirus, non-virus-mediated (e.g., microbubble-enhanced ultrasound, polyplex micelle, RNA interference (siRNA)), or CRISPR (e.g., Cas9).

For some applications, the gene therapy is implemented using techniques described in an article by Takeoka Y et al., entitled, "Gene Therapy Approach for Intervertebral Disc Degeneration: An Update," Neurospine. 2020 March; 17(1): 3-14, which is incorporated herein by reference.

At a gene support step 146, the gene therapy is supported by activating control circuitry 50 to drive intra-pulposus and extra-pulposus exposed electrode surfaces 38 and 42 to electroosmotically drive nutrient-containing fluid into nucleus pulposus 34.

Figure 4:
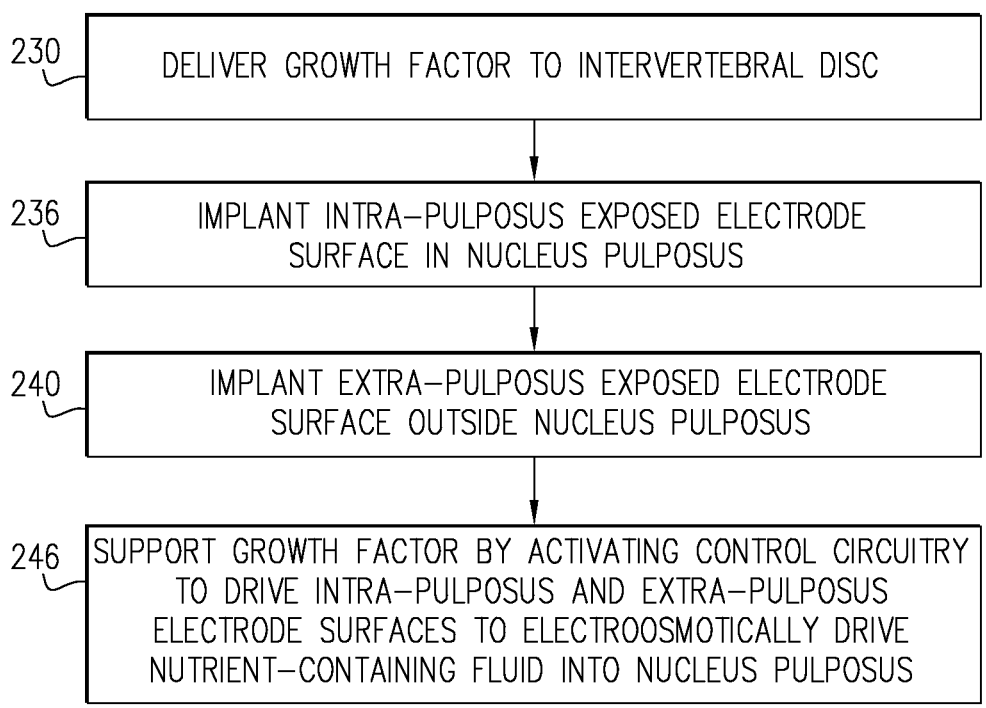
FIG. 4 is a flowchart schematically illustrating yet another method for treating an intervertebral disc, in accordance with some applications of the present invention.

Reference is again made to FIGS. 1A-B, and is additionally made to FIG. 4, which is a flowchart schematically illustrating a method for treating intervertebral disc 20, in accordance with some applications of the present invention. The method of FIG. 4 may be practiced in combination with any of the techniques described hereinabove for the method of FIG. 2, mutatis mutandis.

At a growth factor delivery step 230 of the method, a growth factor is delivered to nucleus pulposus 34 of intervertebral disc 20. For example, the growth factor (e.g., in saline solution) may be injected into nucleus pulposus 34 and/or delivered to nucleus pulposus 34 in other ways, such as described hereinabove with reference to FIG. 1A regarding cells 32 at cell delivery step 30 of the method of FIG. 2, mutatis mutandis. The growth factor may be delivered with or without viral vectors.

At an intra-pulposus electrode implantation step 236, at least one intra-pulposus exposed electrode surface 38 is implanted (typically chronically) in nucleus pulposus 34, such as shown in FIG. 1B.

At an extra-pulposus electrode implantation step 240, at least one extra-pulposus exposed electrode surface 42 is implanted (typically chronically) in body 44 of the subject outside nucleus pulposus 34, as shown in FIG. 1B. For example, extra-pulposus exposed electrode surface 42 may be implanted in a vicinity of an external surface of annulus fibrosus 48 of disc 20, either in physical contact with the external surface or not in physical contact with the external surface.

Alternatively, the at least one extra-pulposus exposed electrode surface 42 is placed outside body 44 of the subject, such as on an external surface of the skin (configuration not shown).

For some applications, the growth factor includes a member of the transforming growth factor-beta (P) superfamily, IGF-1, GDF-5, bone morphogenetic protein (BMP)-2, BMP-7, rhDGF-5, rhGDF-5, anti-NGF (nerve growth factor), or a platelet-derived growth factor. See, for example, Kennon J C et al., "Current insights on use of growth factors as therapy for Intervertebral Disc Degeneration," Biomol Concepts. 2018 May 19; 9(1):43-52.

Optionally, the growth factor is delivered in a liposomal formation, which may provide slow drug delivery over a prolonged period of time. See, for example, Akbarzadeh A et al., "Liposome: classification, preparation, and applications," Nanoscale Res Lett. 2013; 8(1): 102, published online 2013 Feb. 22.

At a growth factor support step 246, the growth factor is supported by activating control circuitry 50 to drive intra-pulposus and extra-pulposus exposed electrode surfaces 38 and 42 to electroosmotically drive nutrient-containing fluid into nucleus pulposus 34.

Figure 5:
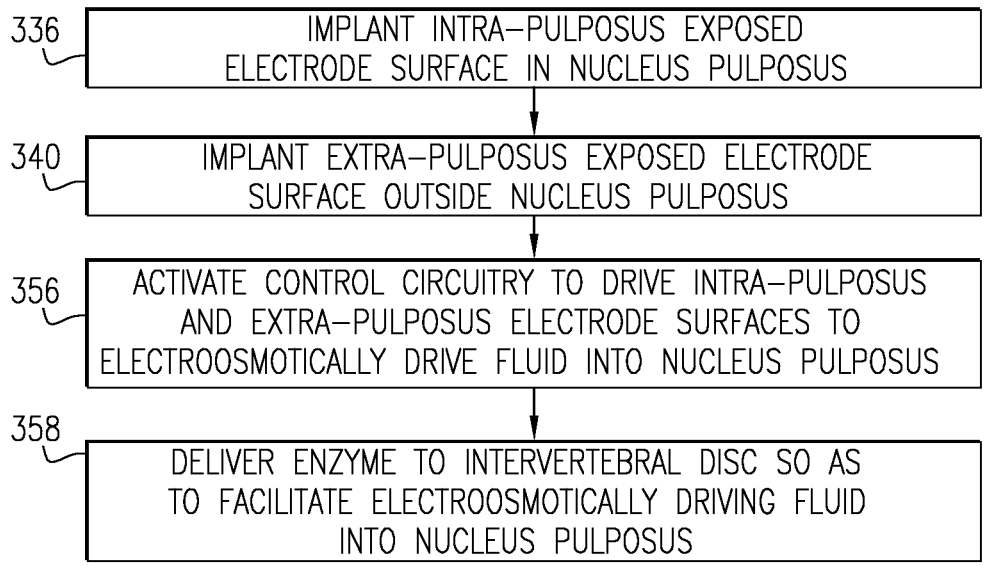
FIG. 5 is a flowchart schematically illustrating still another method for treating an intervertebral disc, in accordance with some applications of the present invention.

Reference is again made to FIGS. 1A-B, and is additionally made to FIG. 5, which is a flowchart schematically illustrating a method for treating intervertebral disc 20, in accordance with some applications of the present invention. The method of FIG. 5 may be practiced in combination with any of the techniques described hereinabove for the method of FIG. 2, mutatis mutandis.

At an intra-pulposus electrode implantation step 336, at least one intra-pulposus exposed electrode surface 38 is implanted (typically chronically) in nucleus pulposus 34, such as shown in FIG. 1B.

At an extra-pulposus electrode implantation step 340, at least one extra-pulposus exposed electrode surface 42 is implanted (typically chronically) in body 44 of the subject outside nucleus pulposus 34, as shown in FIG. 1B. For example, extra-pulposus exposed electrode surface 42 may be implanted in a vicinity of an external surface of annulus fibrosus 48 of disc 20, either in physical contact with the external surface or not in physical contact with the external surface.

Alternatively, the at least one extra-pulposus exposed electrode surface 42 is placed outside body 44 of the subject, such as on an external surface of the skin (configuration not shown).

At an electroosmotic fluid driving step 356, control circuitry 50 is activated to drive intra-pulposus and extra-pulposus exposed electrode surfaces 38 and 42 to electroosmotically drive fluid into nucleus pulposus 34.

At an enzyme delivery step 358, an enzyme is delivered to intervertebral disc 20 or tissue around intervertebral disc 20 so as to facilitate electroosmotically driving the fluid into nucleus pulposus 34. For example, the enzyme (e.g., in saline solution) may be injected into nucleus pulposus 34 and/or delivered to nucleus pulposus 34 in other ways, such as described hereinabove with reference to FIG. 1A regarding cells 32 at cell delivery step 30 of the method of FIG. 2, mutatis mutandis. In applications in which the enzyme is delivered tissue around intervertebral disc 20, some of the enzyme moves (e.g., flows) into nucleus pulposus 34, optionally because of the electroosmotically driving of fluid into nucleus pulposus 34 by activation of control circuitry 50 to drive intra-pulposus and extra-pulposus exposed electrode surfaces 38 and 42, such as described herein.

For example, the enzyme therapy may improve the diffusion of the fluid (and, optionally, molecules in the fluid) into nucleus pulposus 34. For some applications, the enzyme therapy facilitates electroosmotically driving the fluid into nucleus pulposus 34 by decalcifying a vertebral endplate of disc 20 and/or by promoting the porosity of a vertebral endplate, both of which may facilitate inflow of fluid at a lesser resistance.

For some applications, the enzyme includes matrix metalloproteinase-8 (MMP-8), bromelain, and/or papain.

Figure 6:
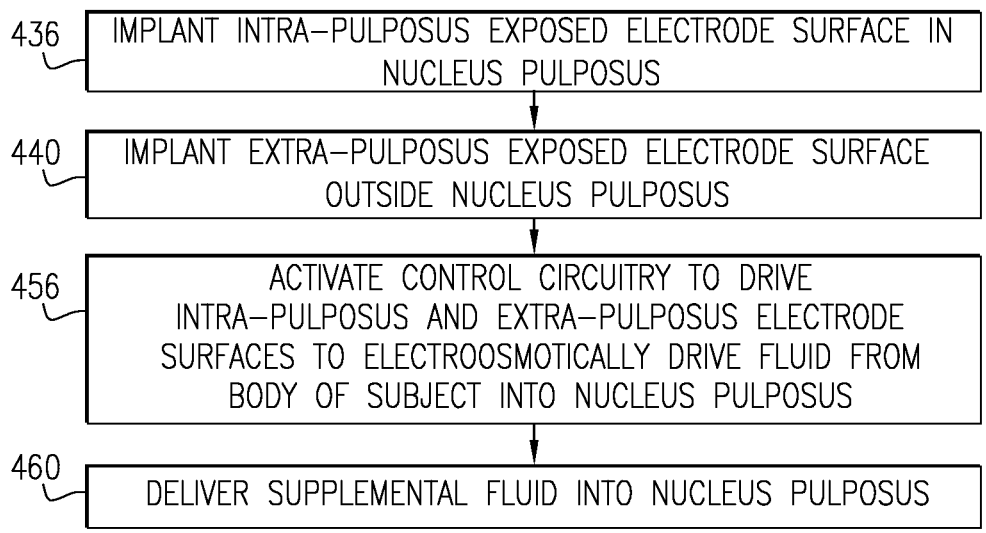
FIG. 6 is a flowchart schematically illustrating another method for treating an intervertebral disc, in accordance with some applications of the present invention.

Reference is again made to FIGS. 1A-B, and is additionally made to FIG. 6, which is a flowchart schematically illustrating a method for treating intervertebral disc 20, in accordance with some applications of the present invention. The method of FIG. 6 may be practiced in combination with any of the techniques described hereinabove for the method of FIG. 2, mutatis mutandis. The method of FIG. 6 may also be practiced in combination with any of the other methods described herein.

At an intra-pulposus electrode implantation step 436, at least one intra-pulposus exposed electrode surface 38 is implanted (typically chronically) in nucleus pulposus 34, such as shown in FIG. 1B.

At an extra-pulposus electrode implantation step 440, at least one extra-pulposus exposed electrode surface 42 is implanted (typically chronically) in body 44 of the subject outside nucleus pulposus 34, as shown in FIG. 1B. For example, extra-pulposus exposed electrode surface 42 may be implanted in a vicinity of an external surface of annulus fibrosus 48 of disc 20, either in physical contact with the external surface or not in physical contact with the external surface.

Alternatively, the at least one extra-pulposus exposed electrode surface 42 is placed outside body 44 of the subject, such as on an external surface of the skin (configuration not shown).

At an electroosmotic fluid driving step 456, control circuitry 50 is activated to drive intra-pulposus and extra-pulposus exposed electrode surfaces 38 and 42 to electroosmotically drive fluid from body 44 of the subject into nucleus pulposus 34, such as to increase pressure in intervertebral disc 20. For example, techniques may be used that are described in one or more of the patent application publications and patents incorporated hereinbelow by reference.

At a supplemental fluid delivery step 460, supplemental fluid is delivered (e.g., injected) to intervertebral disc 20 (nucleus pulposus 34 or annulus fibrosus 48) or tissue surrounding intervertebral disc 20. For example, the supplemental fluid may improve electrical conductivity of disc tissue and provide initial flushing of any high cytokine levels that may occur.

For some applications, delivering (e.g., injecting) the supplemental fluid comprises delivering (e.g., injecting) saline solution to intervertebral disc 20 (nucleus pulposus 34 or annulus fibrosus 48) or tissue surrounding intervertebral disc 20.

For some applications, delivering (e.g., injecting) the supplemental fluid comprises delivering (e.g., injecting) a nutrient-containing fluid to intervertebral disc 20 (nucleus pulposus 34 or annulus fibrosus 48) or tissue surrounding intervertebral disc 20.

For some applications, the supplemental fluid is intermittently injected into intervertebral disc 20 (nucleus pulposus 34 or annulus fibrosus 48) or tissue surrounding intervertebral disc 20 during a plurality of delivery sessions, and control circuitry 50 is activated to intermittently drive, during a plurality of driving sessions, intra-pulposus and extra-pulposus exposed electrode surfaces 38 and 42 to electroosmotically drive the supplemental fluid into nucleus pulposus 34.

For some applications, at supplemental fluid delivery step 460, the supplemental fluid is delivered from a reservoir implanted in body 44 of the subject. Reference is again made to FIGS. 1A-B, and is additionally made to FIG. 7A, which is a flowchart schematically illustrating a method for treating degeneration of intervertebral disc 20, in accordance with some applications of the present invention.

Figure 7A:
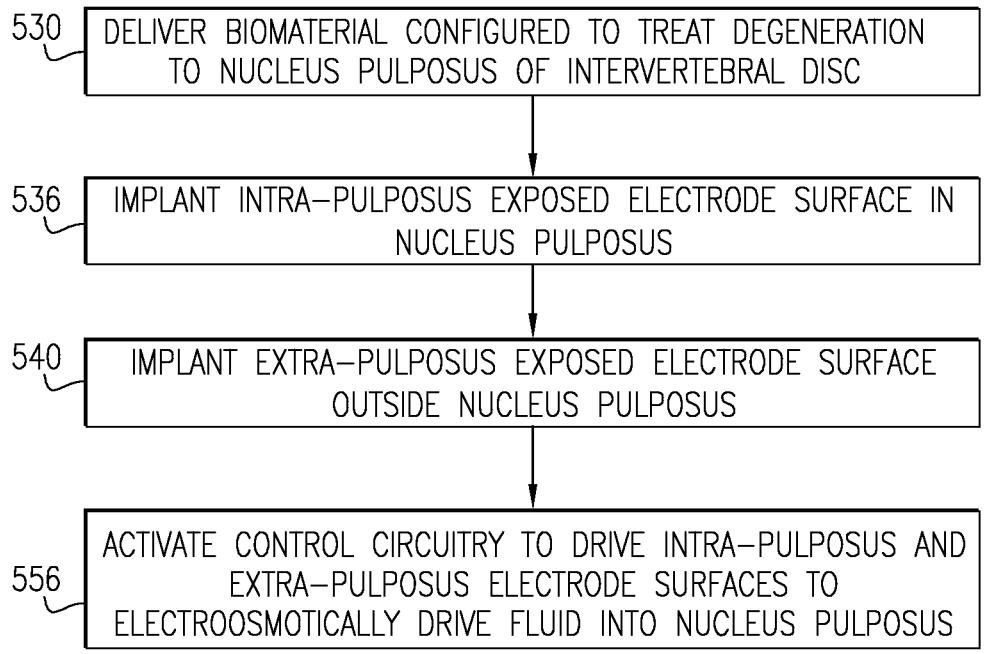
FIGS. 7A-B are flowcharts schematically illustrating yet additional methods for treating an intervertebral disc, in accordance with some respective applications of the present invention.

The method of FIG. 7A may be practiced in combination with any of the techniques described hereinabove for the method of FIG. 2, mutatis mutandis. The method of FIG. 7A may also be practiced in combination with any of the other methods described herein.

At a biomaterial delivery step 530 of the method, a biomaterial configured to treat the degeneration is delivered (e.g., injected) to intervertebral disc 20 (nucleus pulposus 34 or annulus fibrosus 48) or tissue around intervertebral disc 20.

At an intra-pulposus electrode implantation step 536, at least one intra-pulposus exposed electrode surface 38 is implanted (typically chronically) in nucleus pulposus 34, such as shown in FIG. 1B.

At an extra-pulposus electrode implantation step 540, at least one extra-pulposus exposed electrode surface 42 is implanted (typically chronically) in body 44 of the subject outside nucleus pulposus 34, as shown in FIG. 1B. For example, extra-pulposus exposed electrode surface 42 may be implanted in a vicinity of an external surface of annulus fibrosus 48 of disc 20, either in physical contact with the external surface or not in physical contact with the external surface.

Alternatively, the at least one extra-pulposus exposed electrode surface 42 is placed outside body 44 of the subject, such as on an external surface of the skin (configuration not shown).

At an electroosmotic fluid driving step 556, control circuitry 50 is activated to drive intra-pulposus and extra-pulposus exposed electrode surfaces 38 and 42 to electroosmotically drive fluid into nucleus pulposus 34. The biomaterial in intervertebral disc 20 (e.g., nucleus pulposus 34) may enhance the electroosmotic driving of the fluid into nucleus pulposus 34. Typically, the fluid includes nutrient, such as the nutrients described hereinabove with reference to FIGS. 1A-B and 2.

For some applications, the biomaterial includes:
a gel, e.g., a cell-derived matrix gel or a hydrogel,
a structural filler,
a matrix, e.g., an extracellular matrix (ECM),
a polymer, e.g., a protein-based polymer or a synthetic polymer, or
hyaluronic acid.

Injection of hyaluronic acid into the disc has been shown to slow disc degeneration; see, for example, Omlor G W et al., "Injection of a polymerized hyaluronic acid/collagen hydrogel matrix in an in vivo porcine disc degeneration model," Eur Spine J 2012 September; 21(9):1700-8, Epub 2012 Apr. 25.

Figure 7B:
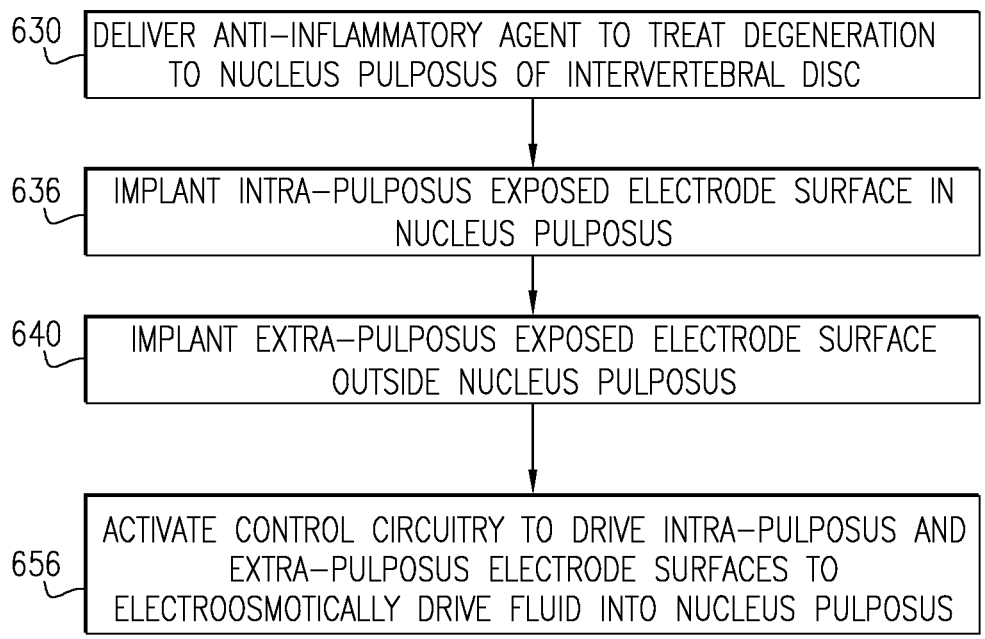

Reference is again made to FIGS. 1A-B, and is additionally made to FIG. 7B, which is a flowchart schematically illustrating a method for treating degeneration of intervertebral disc 20, in accordance with some applications of the present invention.

The method of FIG. 7B may be practiced in combination with any of the techniques described hereinabove for the method of FIG. 2, mutatis mutandis. The method of FIG. 7B may also be practiced in combination with any of the other methods described herein.

At an anti-inflammatory agent delivery step 630 of the method, an anti-inflammatory agent is delivered (e.g., injected) to intervertebral disc 20 (nucleus pulposus 34 or annulus fibrosus 48) or tissue around intervertebral disc 20, in order to treat the degeneration, such as by slowing or halting the degenerative process.

At an intra-pulposus electrode implantation step 636, at least one intra-pulposus exposed electrode surface 38 is implanted (typically chronically) in nucleus pulposus 34, such as shown in FIG. 1B.

At an extra-pulposus electrode implantation step 640, at least one extra-pulposus exposed electrode surface 42 is implanted (typically chronically) in body 44 of the subject outside nucleus pulposus 34, as shown in FIG. 1B. For example, extra-pulposus exposed electrode surface 42 may be implanted in a vicinity of an external surface of annulus fibrosus 48 of disc 20, either in physical contact with the external surface or not in physical contact with the external surface.

Alternatively, the at least one extra-pulposus exposed electrode surface 42 is placed outside body 44 of the subject, such as on an external surface of the skin (configuration not shown).

At an electroosmotic fluid driving step 656, control circuitry 50 is activated to drive intra-pulposus and extra-pulposus exposed electrode surfaces 38 and 42 to electroosmotically drive fluid into nucleus pulposus 34.

For some applications, the anti-inflammatory agent includes:
- platelet rich plasma (PRP),
- curcumin,
- an IL-6 receptor antagonist,
- methylene blue,
- TGF-B1 binding polypeptide, e.g., YH14618 7 peptide amino (Yuhan),
- rhTGFbl, rhCTGF (Notogen),
- NFkB (AnGes),
- A2M (Alpha-2-macroglobulin), or
- anti-TNF-alph.

Injection of hyaluronic acid into the disc has been shown to slow disc degeneration; see, for example, Omlor G W et al., "Injection of a polymerized hyaluronic acid/collagen hydrogel matrix in an in vivo porcine disc degeneration model," Eur Spine J 2012 September; 21(9):1700-8, Epub 2012 Apr. 25.

Reference is now made to FIGS. 1A-7B. For some applications, the techniques described herein are combined with activating control circuitry 50 to drive intra-pulposus and extra-pulposus exposed electrode surfaces 38 and 42 to electroosmotically drive fluid from body 44 of the subject into nucleus pulposus 34, such as to increase pressure in nucleus pulposus 34. For example, techniques may be used that are described in one or more of the patent application publications and patents incorporated hereinbelow by reference. The increase in fluid in nucleus pulposus 34 generally treats or prevents further degeneration of the disc caused at least in part by loss of fluid.

For some applications, control circuitry 50 is activated to:
- repeatedly assume a pressure-increasing mode of operation in alternation with a support mode of operation,
- in the pressure-increasing mode of operation, drive intra-pulposus and extra-pulposus exposed electrode surfaces 38 and 42 to electroosmotically drive fluid from body 44 of the subject into nucleus pulposus 34, such as to increase pressure in nucleus pulposus 34, and
- in the support mode of operation, support the delivered cells, the gene therapy, or the growth factor, as described hereinabove.

For some applications, a housing containing control circuitry 50 is injectable, with an anchor at the proximal end. One or more extra-pulposus exposed electrode surfaces 42 are fixed to an external surface of the housing. For example, the housing may be implanted immediately posterior to the spinal column. For some applications, control circuitry 50 is configured to be implanted subcutaneously, if the housing containing the control circuitry is small. Alternatively, for some applications, control circuitry 50 is configured to be implanted or elsewhere in the subject's body, if the housing of the control circuitry is larger (e.g., includes batteries).

For some applications, control circuitry 50 is driven by an external controller that is in wireless or wired communication with control circuitry 50. For some applications, the external controller is mounted on a bed of the subject (e.g., disposed within a mattress), and is configured to activate control circuitry 50 only at night, and/or only when the subject is sleeping.

For some applications, any of the techniques described herein are combined with injection of a narcotic, such as liposomal bupivacaine or methylene blue, into the disc, to reduce pain; see, for example, Peng B et al., "A randomized placebo-controlled trial of intradiscal methylene blue injection for the treatment of chronic discogenic low back pain," Pain 2010 April; 149(1):124-9.

Reference is made to FIGS. 8 and 9A-J, which are schematic illustrations of a kit 190 and a method for implanting an electrode 200 in nucleus pulposus 34, in accordance with an application of the present invention. Kit 190 comprises electrode 200, a needle 202, and a stylet 206. Electrode 200 (such as distal non-electrically-insulated longitudinal segment 208, described immediately below) may comprise the at least one intra-pulposus exposed electrode surface 38 described hereinabove with reference to FIGS. 1A-7B.

For some applications, electrode 200 comprises coiled wire 204 and a tubular insulator 218 in which coiled wire 204 is partially disposed, with a distal non-electrically-insulated longitudinal segment 208 of coiled wire 204 extending distally out of a distal end of tubular insulator 218, and, typically, a proximal non-electrically-insulated longitudinal segment 210 of coiled wire 204 extending proximally out of a proximal end of tubular insulator 218.

As shown in FIG. 9A, needle 202 is inserted into tissue of a body of a subject and is distally advanced through the tissue into nucleus pulposus 34 of intervertebral disc 20 of the subject, such that (a) a distal longitudinal portion of needle 202, including a distal end of the needle, is positioned within nucleus pulposus 34, and (b) a proximal portion of needle 202, including a proximal end 212 of the needle, remain outside the subject's body.

Figure 9B:
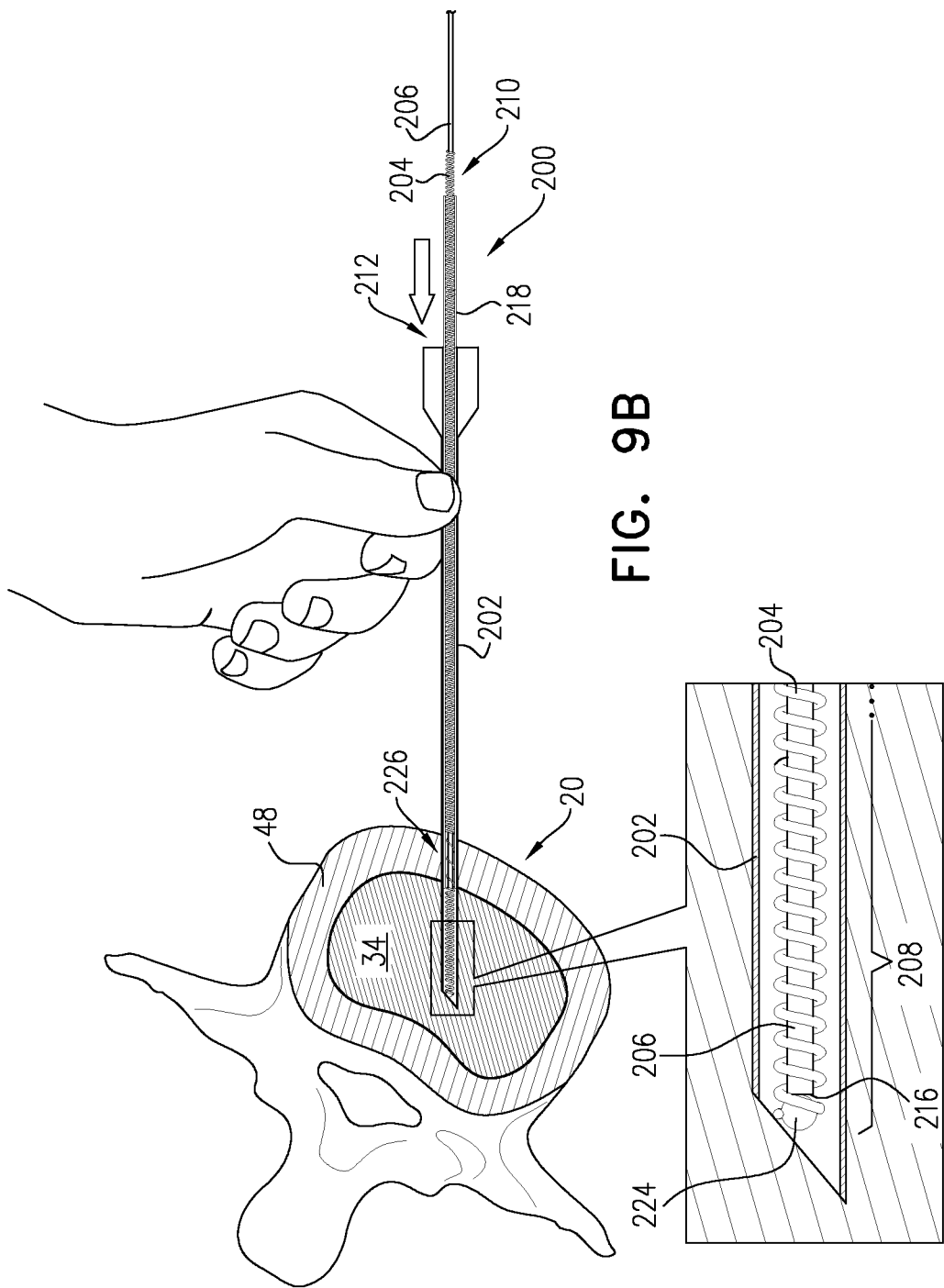
Figure 9C:
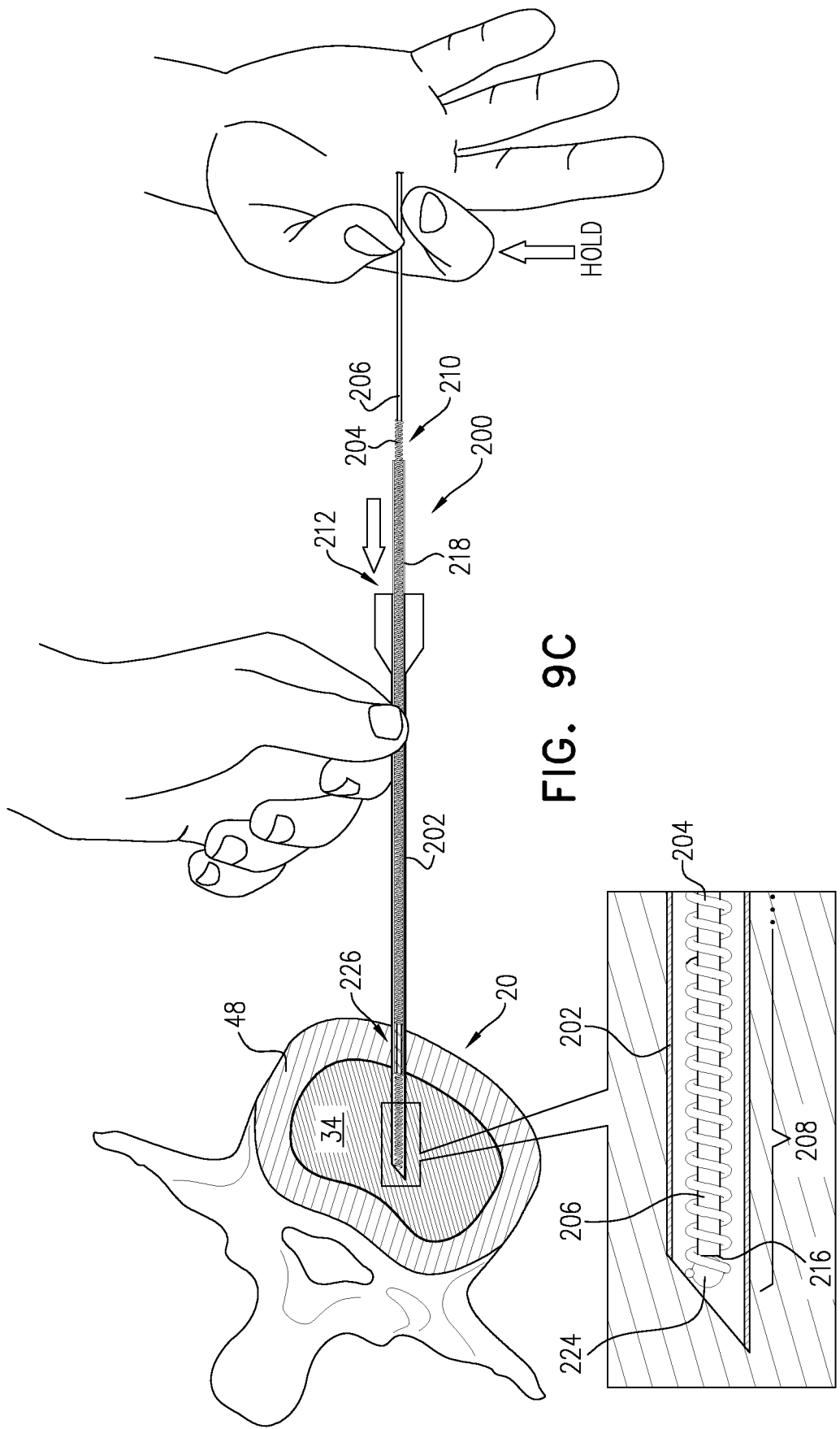
Figure 9D:
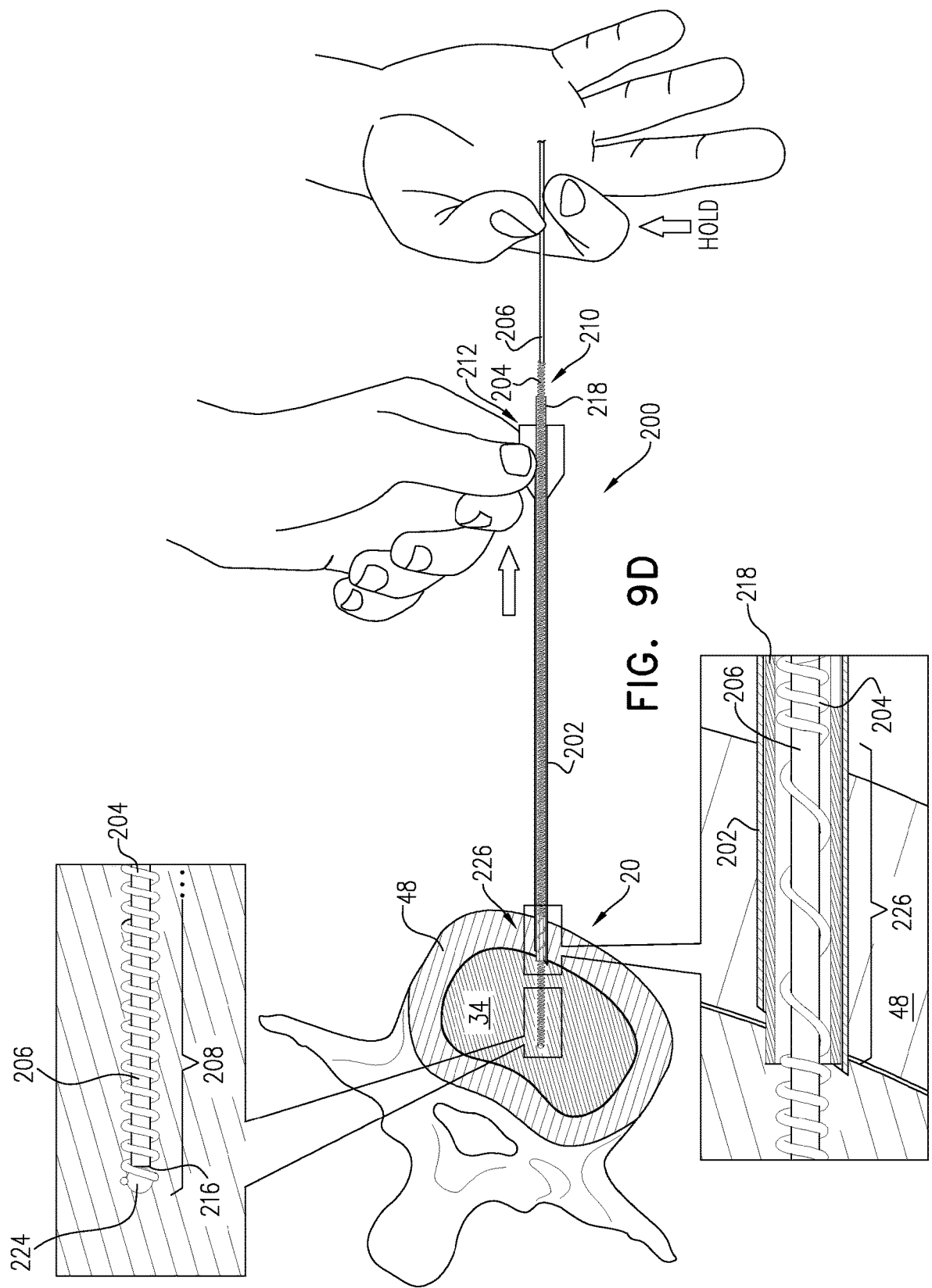
Figure 9E:
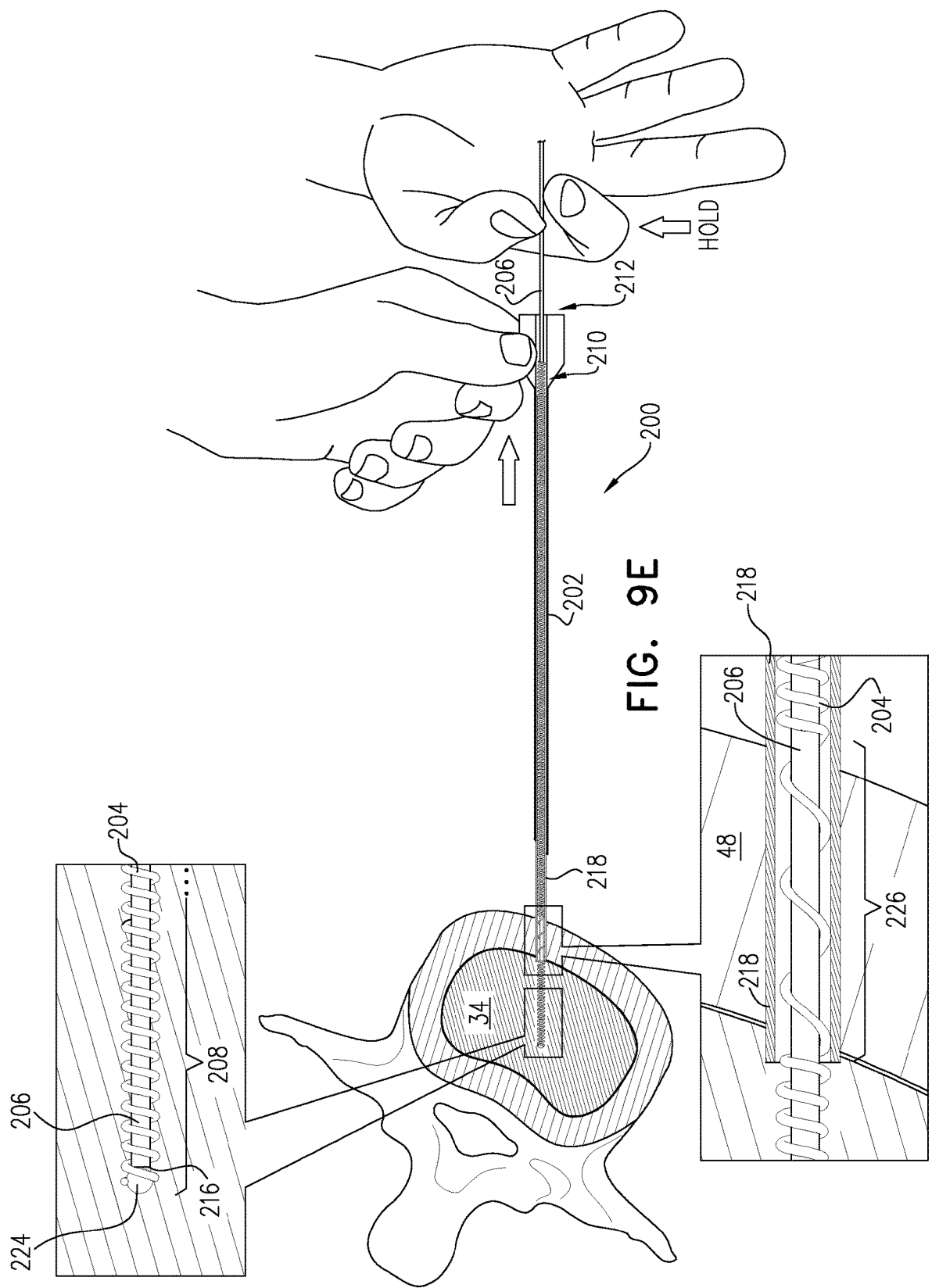
Figure 9F:
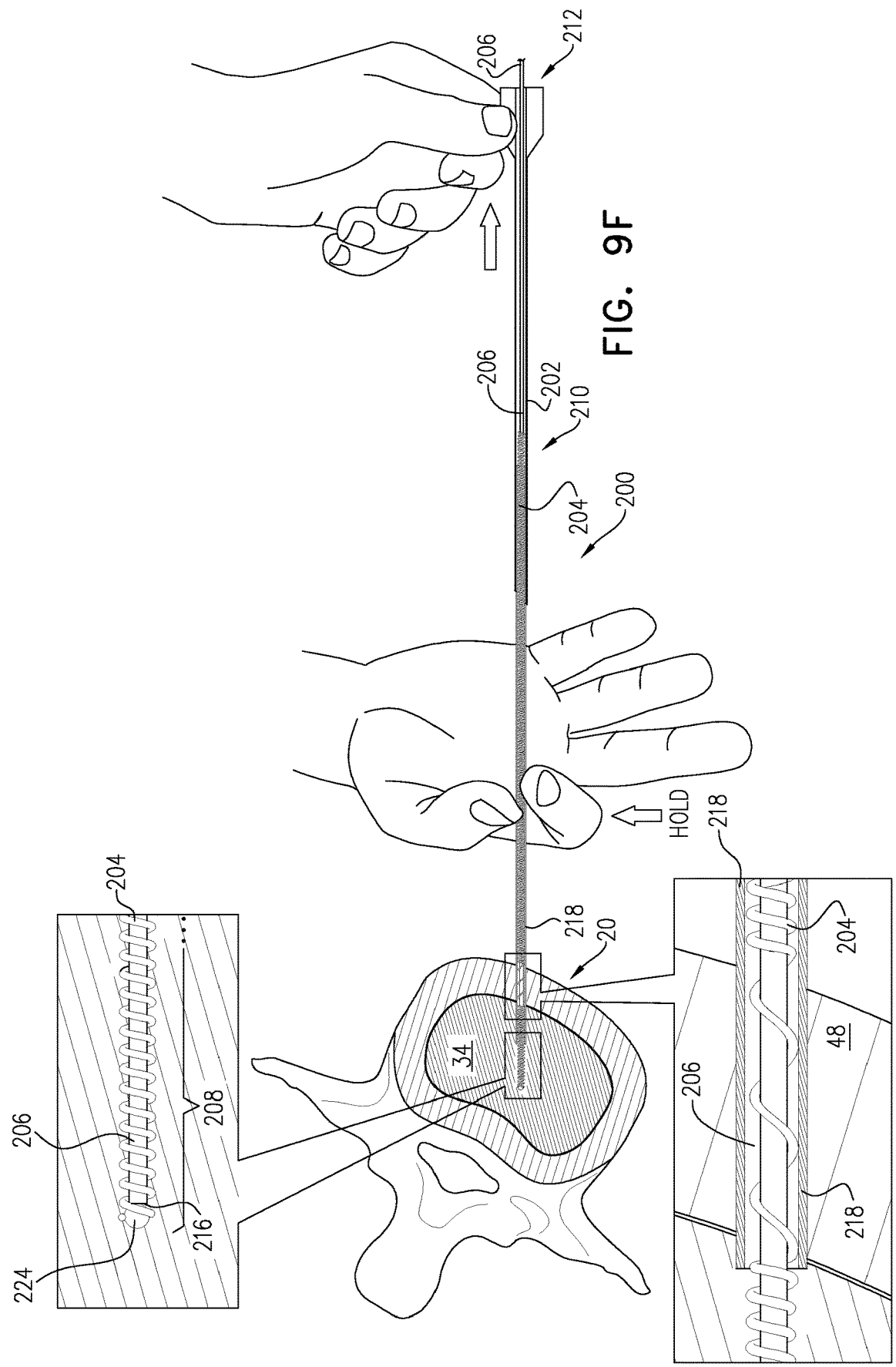
Figure 9G:
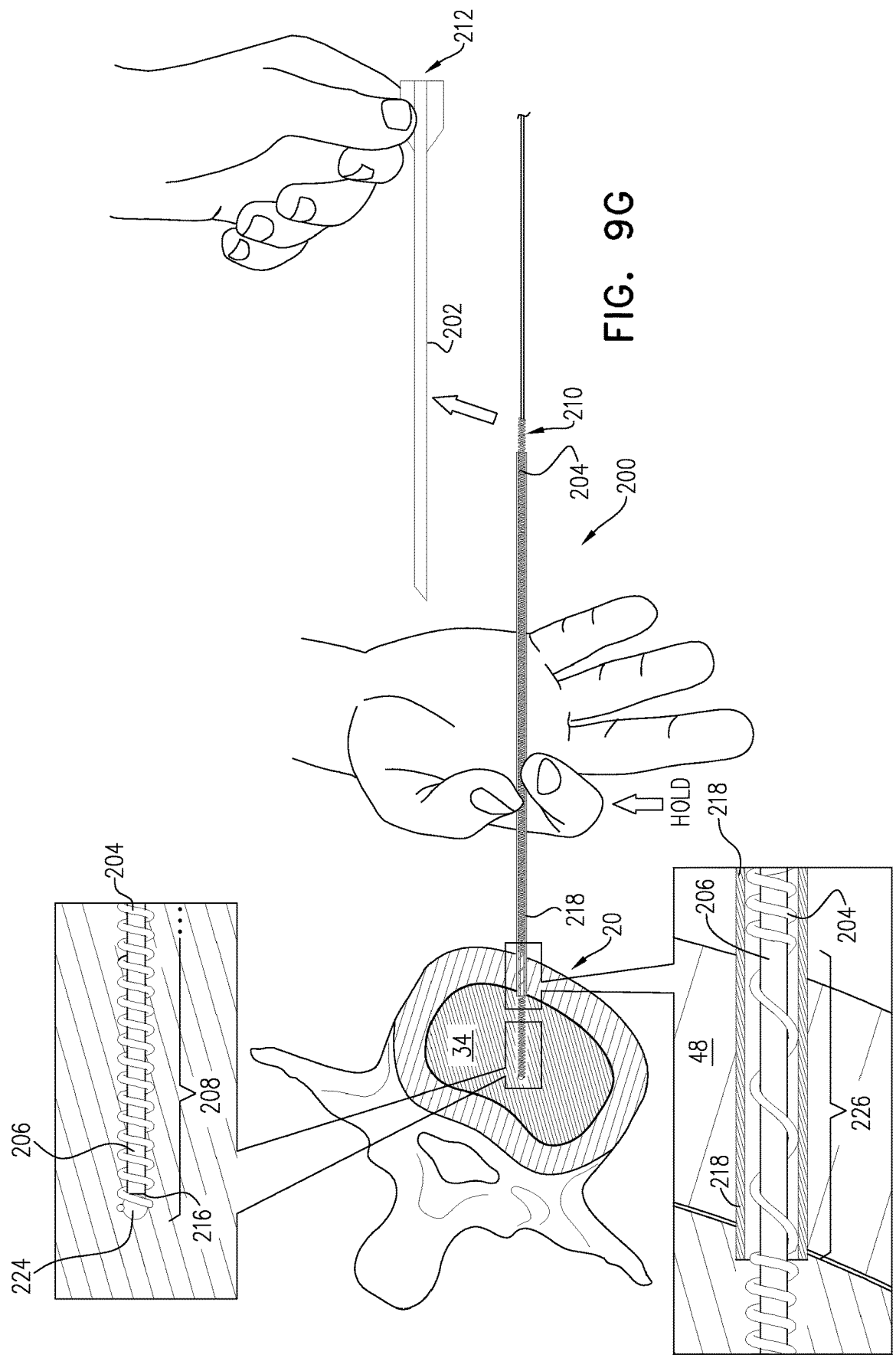

As shown in FIG. 9B, electrode 200 is advanced distally into needle 202 while a stylet 206 is disposed within a longitudinal channel defined by coiled wire 204. Also as shown in FIG. 9B, electrode 200 and stylet 206 are together distally advanced through needle 202 until distal non-electrically-insulated longitudinal segment 208 of coiled wire 204 of electrode 200 and a distal portion of stylet 206, including the distal end of stylet 206, is positioned within nucleus pulposus 34. Stylet 206, needle 202, and coiled wire 204 remain partially outside the subject's body, with stylet 206 and coiled wire 204 extending proximally out of proximal end 212 of needle 202.

Stylet 206 generally reinforces and stiffens coiled wire 204, in order to enable coiled wire 204 to better withstand bending forces during delivery, despite the low natural pushability of coiled wire 204 because of its high flexibility, and the radial gap between coiled wire 204 and the inner surface of needle 202. Stylet 206 also aids with handling electrode 200 prior to injection, by protecting the electrode from unintentional bending that might damage the electrode.

For some applications, stylet 206 comprises a cobalt chrome material or stainless steel, which optionally is thermally treated in order to harden the material while remain sufficiently flexible. These materials may enable good pushability even in configuration in which the stylet is very narrow, such as a 0.008" diameter. Alternatively or additionally, stylet 206 may can undergo an electropolishing process to reduce friction.

As shown in FIGS. 9C-G, thereafter, while stylet 206 is held axially stationary with respect to nucleus pulposus 34, needle 202 is proximally withdrawn from the subject's body, leaving distal non-electrically-insulated longitudinal segment 208 of coiled wire 204 within nucleus pulposus 34, with a distal end 216 of stylet 206 within the longitudinal channel of coiled wire 204, including within distal non-electrically-insulated longitudinal segment 208.

Because stylet 206 serves as an internal support for electrode 200, which is typically highly flexible, stylet 206 serves as a supportive structure for fine-tuning placement of electrode 200 after needle 202 has been withdrawn, in addition to aiding with pushing the electrode distally during exchange with needle 202.

Figure 9I:
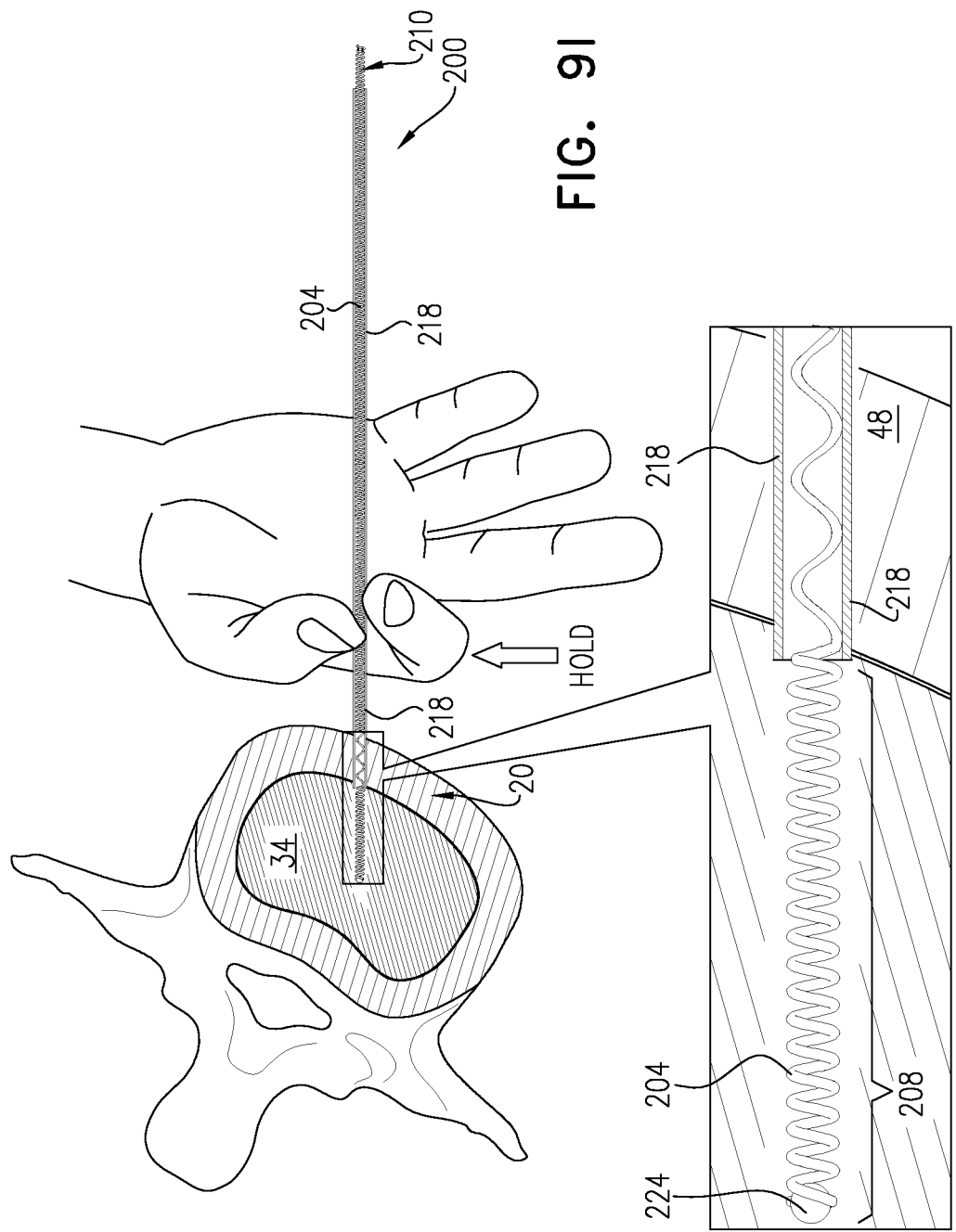
Figure 9J:
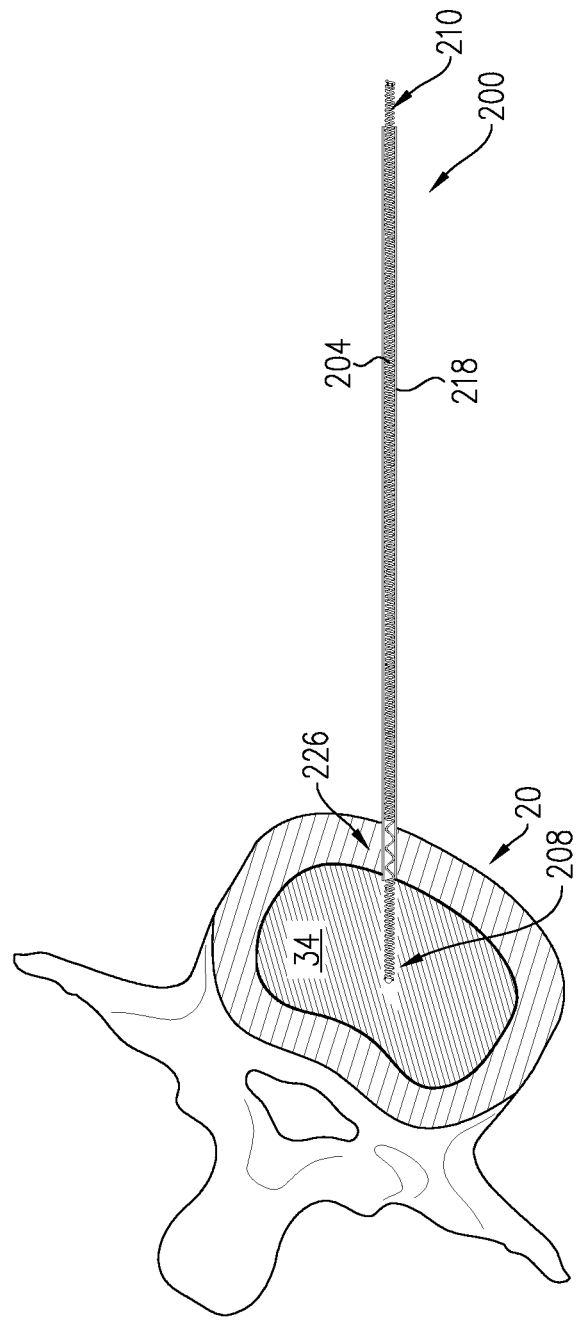

As shown in FIG. 9H, stylet 206 is proximally withdrawn from the subject's body and from the longitudinal channel of coiled wire 204, while leaving distal non-electrically-insulated longitudinal segment 208 of coiled wire 204 within nucleus pulposus 34, as shown in FIGS. 9I-J.

For some applications, distally advancing needle 202 through the tissue into nucleus pulposus 34 as shown in FIG. 9A, comprises distally advancing needle 202 through the tissue into nucleus pulposus 34 while distal non-electrically-insulated longitudinal segment 208 of coiled wire 204 is constrained only by needle 202 and stylet 206.

For some applications in which electrode 200 comprises tubular insulator 218, proximally withdrawing needle 202, as shown in FIGS. 9C-G, comprises proximally withdrawing needle 202 while leaving (a) distal non-electrically-insulated longitudinal segment 208 of coiled wire 204 within nucleus pulposus 34, and (b) tubular insulator 218 at least partially within the subject's body, at least partially outside nucleus pulposus 34. Optionally, a distal portion of tubular insulator 218 is left at least partially disposed within annulus fibrosus 48.

For some applications, coiled wire 204 of electrode 200 is coated with a friction-reducing coating (e.g., PTFE or ePTFE), such as to reduce friction during proximal withdrawal of stylet 206. Alternatively or additionally, coiled wire 204 of electrode 200 is coated with a medical grade material, such as a thin layer of silicone or PEBA.

For some applications, needle 202 includes a plurality of radiopaque markers, and distally advancing needle 202 through the tissue into nucleus pulposus 34, as shown in FIG. 9A, comprises observing the radiopaque markers to confirm that the distal longitudinal portion of needle 202 is disposed in nucleus pulposus 34. For example, the plurality of radiopaque markers may be arranged as a ruler along needle 202. Alternatively or additionally, the radiopacity of stylet 206 and/or distal-most non-coiled tip 214, described hereinabove, and/or optional radiopaque markers coupled to stylet 206 may help the physician assess the length of the portion of electrode 200 that is to be injected (because electrode 200 itself is typically not particularly radiopaque).

For some applications, electrode 200 includes a distal-most non-coiled tip 224, which is disposed at a distal end of coiled wire 204, and which is shaped so as to define a proximally-facing surface. For some of these applications, distal-most non-coiled tip 214 is shaped so as to define an atraumatic distally-facing end surface, which increases the electrical contract surface area. For some applications, the atraumatic distally-facing end surface is spherical (as shown) or semi-spherical (configuration not shown). For some applications, distal-most non-coiled tip 224 is electrically conductive and is coupled in electrical communication with coiled wire 204. In addition, distal-most non-coiled tip 214 may serve to prevent stylet 206 from exiting the distal end of coiled wire 204, and/or to allow the physician to push electrode 200 forward from the electrode's distal end by pushing stylet 206 against distal-most non-coiled tip 214 from within coiled wire 204. Optionally, distal-most non-coiled tip 214 comprises a metal, such as titanium, such as a radiopaque metal.

Reference is again made to FIG. 8. For some applications, coiled wire 204 is shaped so as to define an intra-annular longitudinal segment 226 that has a greater pitch than respective pitches of portions of coiled wire 204 immediately proximal and distal to intra-annular longitudinal segment 226. For example, the pitch of intra-annular longitudinal segment 226 may be at least 2 times, such as least 4 times, the respective pitches of the portions of coiled wire 204 immediately proximal and distal to intra-annular longitudinal segment 226, and/or the pitch of intra-annular longitudinal segment 226 may be between 0.5 and 1.5 mm, such as between 0.75 and 1.25 mm, e.g., 1 mm. Typically, intra-annular longitudinal segment 226 has a length of between 0.8 and 1 mm. Typically, intra-annular longitudinal segment 226 is disposed within tubular insulator 218.

For example, the pitch of distal non-electrically-insulated longitudinal segment 208 may be between 0.1 and 0.15 mm.

For example, the pitch of the portion of coiled wire 204 proximal to intra-annular longitudinal segment 226 may be between 0.2 and 0.3 mm.

The respective pitches of distal non-electrically-insulated longitudinal segment 208 and the portion of coiled wire 204 proximal to intra-annular longitudinal segment 226 may be the same as or different from each other.

Reference is again made to FIG. 9J. Typically, annulus fibrosus 48 squeezes the longitudinal portion of electrode 200 disposed within annulus fibrosus 48. Tissue of the annulus fibrosus generally protrudes between turns of coiled wire 204, typically by pressing, between turns of coiled wire 204, the thin wall of a portion of tubular insulator 218 that surrounds the longitudinal portion of electrode 200 disposed within annulus fibrosus 48, thereby:

creating a good seal between the annulus fibrosus and the electrode, thereby inhibiting flow of liquid and/or biological matter in and out of the nucleus pulposus, and/or anchoring (fixing) the electrode to the annulus fibrosus and disc, such that a separate fixation element (such as a suture or clip) is typically not required to hold the electrode in place with respect to the annulus fibrosus or disc.

Tubular insulator 218 typically comprises a material that is configured to remain intact, such as for long-term delivery of fluid.

For some applications, the thin wall of the portion of tubular insulator 218 that surrounds the longitudinal portion of electrode 200 disposed within annulus fibrosus 48 has a thickness of between 0.02 and 0.07 mm (between 0.001" and 0.003").

Reference is still made to FIG. 9J. For some applications, upon implantation of electrode 200, intra-annular longitudinal segment 226 is at least partially disposed within annulus fibrosus 48, typically surrounded by a distal portion of tubular insulator 218. The greater pitch of intra-annular longitudinal segment 226 generally reduces the radial strength of coiled wire 204, thereby allowing annulus fibrosus 48 to naturally squeeze the coiled portion more tightly, thereby improving sealing and/or anchoring between the electrode and the annulus fibrosus upon removal of stylet 206.

Figure 10:
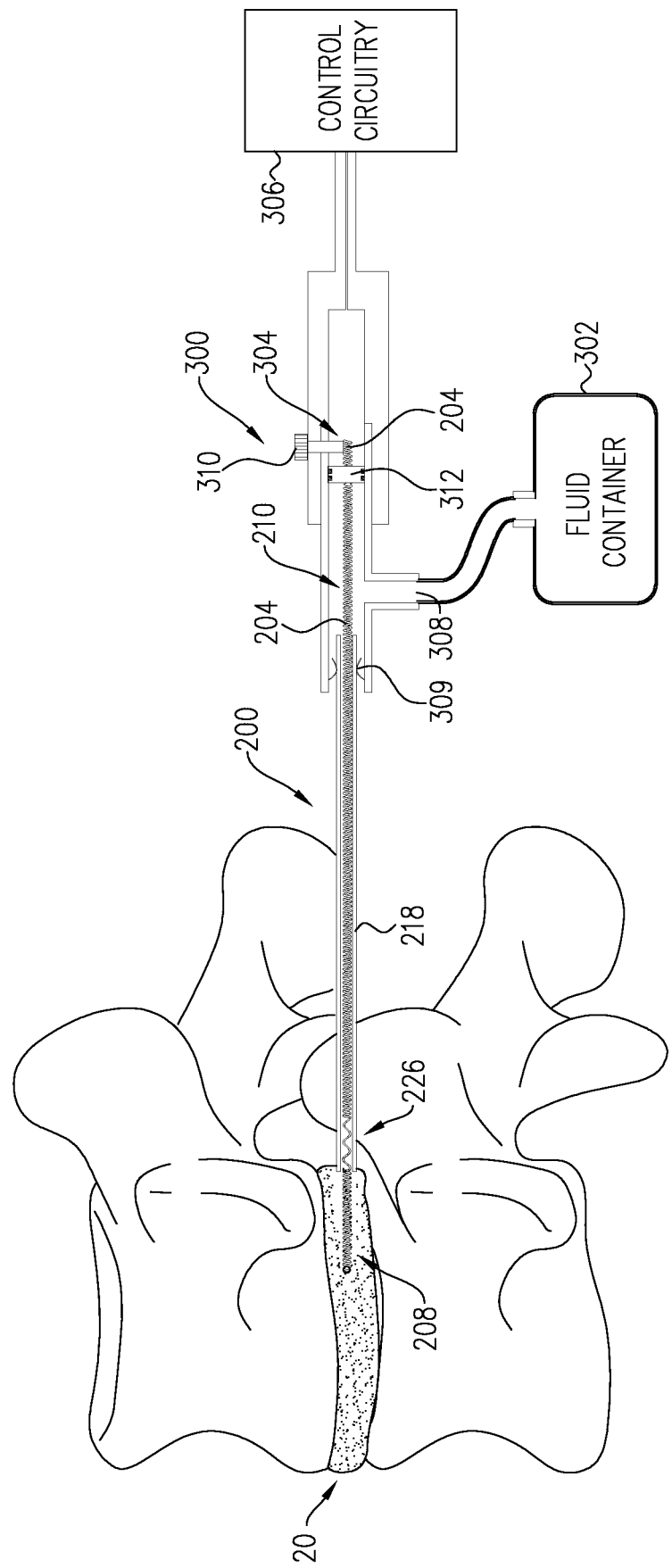
FIG. 10 is a schematic illustration of a connector, in accordance with an application of the present invention.

Reference is now made to FIG. 10, which is a schematic illustration of a connector 300, in accordance with an application of the present invention. Connector 300 is typically configured to be couplable to a proximal portion of electrode 200, or another type of electrode, upon completion of implantation of the electrode. Connector 300 provides:
- a fluid flow path between an external fluid container 302 and a channel defined by tubular insulator 218 between connector 300 and a distal end of tubular insulator 218 disposed within nucleus pulposus 34, and
- an electrical connection 304 between coiled wire 204 and control circuitry 306.

Connector 300 is shaped so as to define:
- a fluid port 308, for example through a lateral wall of connector 300, for connection to fluid container 302, and
- an electrode connector port 309, which is configured to provide a liquid-tight seal with tubular insulator 218.

The fluid flow path may be either one-way or two-way.

For example, connector 300 may comprise a conductive screw 310 that is configured to make electrical connection 304.

Optionally, connector 300 comprises a seal 312 to prevent fluid communication between the channel of tubular insulator 218 and connection 304.

For some applications, connector 300 is used to deliver any of the fluids, cells, or other materials described hereinabove to nucleus pulposus 34. Connector 300 may be used temporarily soon after implantation of the electrode, and then decoupled from the electrode, or may be permanently attached to the electrode, and thus may be implantable in the body of the subject, as may be fluid container 302 (e.g., with a self-sealing subcutaneous port for refilling).

Optionally, if the channel within tubular insulator 218 should become blocked over time (such as by fluids, blood, or tissue), a flexible stylet is inserted into channel to clear the channel before delivery of liquid or other materials through the channel.

In some applications of the present invention, the techniques and apparatus described herein are combined with techniques and apparatus described in one or more of the following applications, which are assigned to the assignee of the present application and are incorporated herein by reference:

U.S. Pat. No. 8,577,469 to Gross;
U.S. Pat. No. 9,731,122 to Gross;
U.S. Pat. No. 9,770,591 to Gross et al.;
U.S. Pat. No. 9,950,156 to Gross et al.;
U.S. Pat. No. 10,518,085 to Gross et al.; and/or
US Patent Application Publication 2021/0059830 to Gross It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for treating an intervertebral disc of a subject, the method comprising:
   - delivering a growth factor to a nucleus pulposus of the intervertebral disc by injecting the growth factor through a hollow needle;
   - implanting at least one intra-pulposus exposed electrode surface in the nucleus pulposus;
   - implanting at least one extra-pulposus exposed electrode surface in a body of the subject outside the nucleus pulposus; and
   - supporting the growth factor by activating control circuitry to drive the intra-pulposus and the extra-pulposus exposed electrode surfaces to electroosmotically drive nutrient-containing fluid into the nucleus pulposus.

2. The method according to claim 1, wherein delivering the growth factor to the nucleus pulposus comprises injecting the growth factor into the nucleus pulposus through the hollow needle.

3. The method according to claim 1, wherein delivering the growth factor to the nucleus pulposus comprises delivering the growth factor to the body of the subject outside the nucleus pulposus such that the growth factor moves into the nucleus pulposus.

4. The method according to claim 3, wherein delivering the growth factor to the body of the subject outside the nucleus pulposus comprises delivering the growth factor to an annulus fibrosus of the intervertebral disc such that the growth factor moves into the nucleus pulposus.

5. The method according to claim 3, wherein delivering the growth factor to the nucleus pulposus comprises, while at least some of the growth factor is outside the nucleus pulposus, activating the control circuitry to drive the intra-pulposus and the extra-pulposus exposed electrode surfaces to electroosmotically drive the growth factor into the nucleus pulposus.

6. The method according to claim 1, wherein supporting the growth factor comprises supporting the growth factor by activating the control circuitry to apply, between the intra-pulposus exposed electrode surface and the extra-pulposus exposed electrode surface, a mean voltage insufficient to cause electrolysis.

7. The method according to claim 1, wherein the nutrient-containing fluid includes oxygen, and wherein supporting the growth factor comprises supporting the growth factor by activating the control circuitry to drive the intra-pulposus and the extra-pulposus exposed electrode surfaces to electroosmotically drive the oxygen-containing fluid into the nucleus pulposus.

8. The method according to claim 1, wherein the nutrient-containing fluid includes glucose, and wherein supporting the growth factor comprises supporting the growth factor by activating the control circuitry to drive the intra-pulposus and the extra-pulposus exposed electrode surfaces to electroosmotically drive the glucose-containing fluid into the nucleus pulposus.

9. The method according to claim 1, wherein supporting the growth factor comprises supporting the growth factor by activating the control circuitry to intermittently drive, during a plurality of sessions, the intra-pulposus and the extra-pulposus exposed electrode surfaces to electroosmotically drive the nutrient-containing fluid into the nucleus pulposus.

10. The method according to claim 9, wherein an average duration of non-activation periods between sequential ones of the sessions is at least 12 hours.

11. The method according to claim 9, wherein the plurality of sessions includes at least 10 sessions.

12. The method according to claim 9, wherein supporting the growth factor comprises supporting the growth factor by activating the control circuitry to intermittently drive the intra-pulposus and the extra-pulposus exposed electrode surfaces to electroosmotically drive the nutrient-containing fluid into the nucleus pulposus during one or more of the sessions during each 24-hour period.

13. The method according to claim 12, wherein supporting the growth factor comprises supporting the growth factor by activating the control circuitry to intermittently drive the intra-pulposus and the extra-pulposus exposed electrode surfaces to electroosmotically drive the nutrient-containing fluid into the nucleus pulposus during exactly one of the sessions during each 24-hour period.

14. The method according to claim 9, wherein the plurality of sessions extends over at least one week.

15. The method according to claim 1, wherein supporting the growth factor comprises supporting the growth factor by activating the control circuitry to apply direct current between the intra-pulposus and the extra-pulposus exposed electrode surfaces.

* * * * *